US012788740B2

(12) United States Patent
Tanzi et al.

(10) Patent No.: US 12,788,740 B2
(45) Date of Patent: Nov. 10, 2026

(54) COMPOSITIONS FOR TREATING NEURODEGENERATIVE DISEASES

(71) Applicant: The General Hospital Corporation, Boston, MA (US)

(72) Inventors: Rudolph E. Tanzi, Hull, MA (US); Doo Yeon Kim, Boston, MA (US); Ana Griciuc, Arlington, MA (US); Luisa Quinti, Charlestown, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 19/365,074

(22) Filed: Oct. 21, 2025

(65) Prior Publication Data

US 2026/0191821 A1 Jul. 9, 2026

Related U.S. Application Data

(63) Continuation of application No. 19/153,936, filed as application No. PCT/US2024/014677 on Feb. 6, 2024.

(60) Provisional application No. 63/512,012, filed on Jul. 5, 2023, provisional application No. 63/443,690, filed on Feb. 6, 2023.

(51) Int. Cl.

| | |
|---|---|
| ***A61K 31/366*** | (2006.01) |
| ***A61K 31/352*** | (2006.01) |
| ***A61P 25/28*** | (2006.01) |
| ***A61P 29/00*** | (2006.01) |

(52) U.S. Cl.
CPC .......... *A61K 31/366* (2013.01); *A61K 31/352* (2013.01); *A61P 25/28* (2018.01); *A61P 29/00* (2018.01)

(58) Field of Classification Search
None
See application file for complete search history.

(56) References Cited

U.S. PATENT DOCUMENTS

| | | | |
|---|---|---|---|
| 11,591,305 | B2 | 2/2023 | Kang et al. |
| 2009/0326057 | A1 | 12/2009 | Seeram et al. |
| 2010/0105630 | A1 | 4/2010 | Blagg |
| 2010/0189653 | A1 | 7/2010 | Robbins et al. |
| 2020/0397807 | A1 | 12/2020 | Pranesh et al. |
| 2021/0330611 | A1 | 10/2021 | Akassoglou et al. |
| 2021/0332139 | A1 | 10/2021 | Constantin |
| 2021/0353591 | A1 | 11/2021 | Rinsch et al. |

FOREIGN PATENT DOCUMENTS

| | | | | |
|---|---|---|---|---|
| CN | 106109536 | B | 10/2019 | |
| WO | WO 2006/105196 | A2 | 10/2006 | |
| WO | WO 2010/078659 | A1 | 7/2010 | |
| WO | WO-2018079715 | A1 * | 5/2018 | A61K 31/121 |
| WO | WO 2018/207952 | A1 | 11/2018 | |
| WO | WO 2019/168972 | A1 | 9/2019 | |

OTHER PUBLICATIONS

Ali et al., "Recommendations for Anti-inflammatory Treatments in Alzheimer's Disease: A Comprehensive Review of the Literature," Cureus, May 2019, 11(5):e4620, 6 pages.
CAS No. 1143-70-0, "Urolithin A," Sigma-Aldrich, retrieved on Nov. 18, 2025, retrieved from URL <https://www.sigmaaldrich.com/IN/en/product/sigma/sml1791>, 5 pages.
CAS No. 528-48-3, "Fisetin," Sigma-Aldrich, retrieved on Nov. 18, 2025, retrieved from URL <https://www.sigmaaldrich.com/IN/en/product/sial/ph182542>, 4 pages.
Deacon, "Assessing nest building in mice," Nature Protocols, Aug. 2006, 1(3):1117-1119.
Esselun et al., "Effects of Urolithin A on Mitochondrial Parameters in a Cellular Model of Early Alzheimer Disease," International Journal of Molecular Sciences, Aug. 2021, 22(15):8333, 19 pages.
Grynkiewicz et al., "New Perspectives for Fisetin," Frontiers in Chemistry, Oct. 2019, 7:697, 10 pages.
Gyengesi et al., "In search of an anti-inflammatory drug for Alzheimer disease," Nature Reviews, Neurology, Mar. 2020, 16(3):131-132.
Hassan et al., "The neuroprotective effects of fisetin, a natural flavonoid in neurodegenerative diseases: Focus on the role of oxidative stress," Frontiers in Pharmacology, Oct. 2022, 13:1015835, 30 pages.
Hickman et al., "Microglial Dysfunction and Defective β-Amyloid Clearance Pathways in Aging Alzheimer's Disease Mice," The Journal of Neuroscience, Aug. 2008, 28(33):8354-8360.
International Preliminary Report on Patentability in International Appln. No. PCT/US2024/014677, mailed on Aug. 21, 2025, 7 pages.
International Search Report and Written Opinion in International Appln. No. PCT/US2024/014677, mailed on May 9, 2024, 16 pages.
International Search Report and Written Opinion in International Appln. No. PCT/US2025/040545, mailed on Nov. 24, 2025, 19 pages.
Invitation to Pay Additional Fees in International Appln. No. PCT/US2025/040545, mailed on Sep. 29, 2025, 2 pages.
Noshadi et al., "Synthesis, Characterization, Molecular Docking, and Biological Activities of Some Natural and Synthetic Urolithin Analogs," Chemistry & Biodiversity, Aug. 2020, 17(8):e2000197, 13 pages.
Office Action in Eurasian Appln. No. 202592315, mailed on Dec. 8, 2025, 8 pages (with English translation).
Ransohoff et al., "The myeloid cells of the central nervous system parenchyma," Nature, Nov. 2010, 468(7321):253-262.

(Continued)

*Primary Examiner* — Sarah Pihonak
*Assistant Examiner* — Donna M Nestor
(74) *Attorney, Agent, or Firm* — Fish & Richardson P.C.

(57) ABSTRACT

Provided herein are methods and compositions utilizing a urolithin A agent and a fisetin agent for treatment of neurodegenerative diseases.

17 Claims, 18 Drawing Sheets

(56) References Cited

OTHER PUBLICATIONS

Roy et al., "Synthesis, inverse docking-assisted identification and in vitro biological characterization of Flavonol-based analogs of fisetin as c-Kit, CDK2 and mTOR inhibitors against melanoma and non-melanoma skin cancers," Bioorganic Chemistry, Feb. 2021, 107:104595, 53 pages (Author Manuscript).
Salter et al., "Microglia emerge as central players in brain disease," Nature Medicine, Sep. 2017, 23(9):1018-1027.
Selma et al., "Description of urolithin production capacity from ellagic acid of two human intestinal Gordonibacter species," Food and Function, May 2014, 5(8): 1779-1784.
Sevigny et al., "The antibody aducanumab reduces Aβ plaques in Alzheimer's disease," Nature, Aug. 2016, 537(7168):50-56.
Singh et al., "Urolithin A improves muscle strength, exercise performance, and biomarkers of mitochondrial health in a randomized trial in middle-aged adults," Cell Reports Medicine, May 2022, 3(5):100633, 12 pages.
Yuksel et al., "Aducanumab for Alzheimer's Disease: Summarized Data From Emerge, Engage, and Prime Studies," The Senior Care Pharmacist, Aug. 2022, 37(8):329-334.
alzheimersweekly.com [online], "Harvard's Dr. Tanzi Develops CogniSHIELD Brain Supplement," Aug. 1, 2025, URL <https://alzheimersweekly.com/harvards-dr-tanzi-develops-cognishield-brain-supplement/>, retrieved on May 19, 2026, 13 pages.
Ballesteros-Alvarez et al., "Urolithin A reduces amyloid-beta load and improves cognitive deficits uncorrelated with plaque burden in a mouse model of Alzheimer's disease," GeroScience, 2023, 45:1095-1113.
Ghareeb et al., "Efficacy of Natural Extracts of Ginkgo Biloba and Berberry and a Synthetic Derivative of Genistein (ipriflavone), as Acetylcholinesterase Inhibitors, Comparative Study with Aricept® effect," Journal of Biochemistry and Biotechnology, Jan.-Jun. 2010, 1(1):5-11.
International Search Report and Written Opinion in International Appln. No. PCT/US2025/040551, mailed on Dec. 22, 2025, 13 pages.
International Search Report and Written Opinion in Intl. Appln. No. PCT/US2025/040532, mailed on Dec. 4, 2025, 12 pages.

* cited by examiner

FIG. 2B
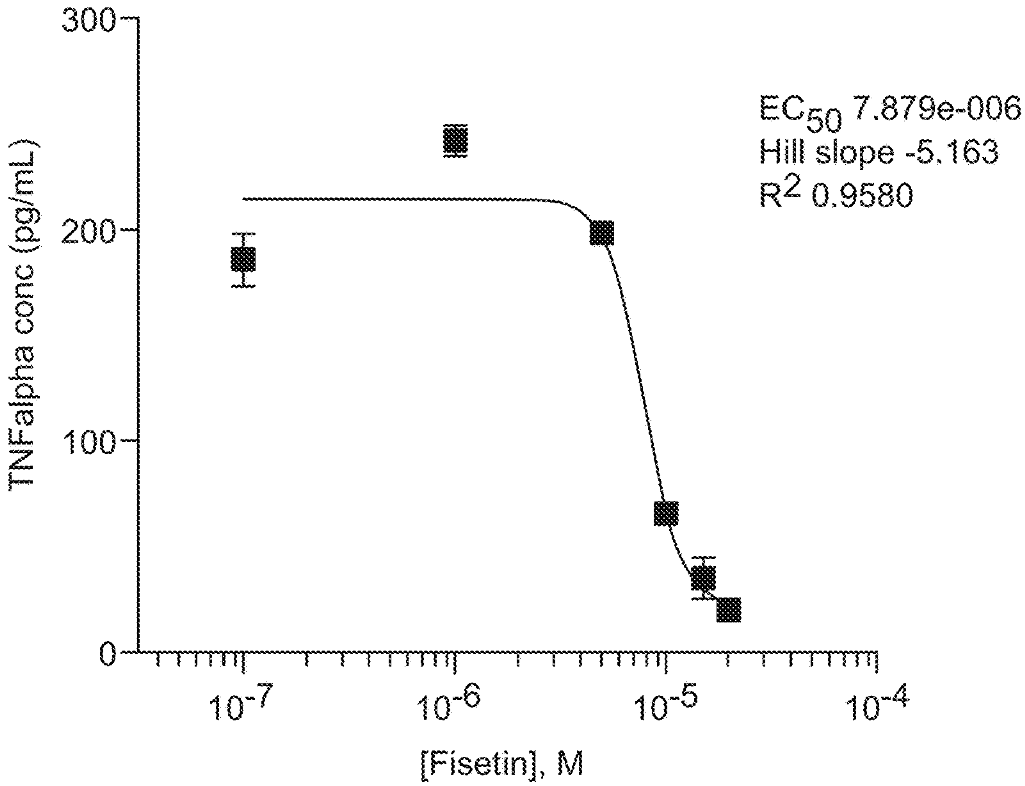
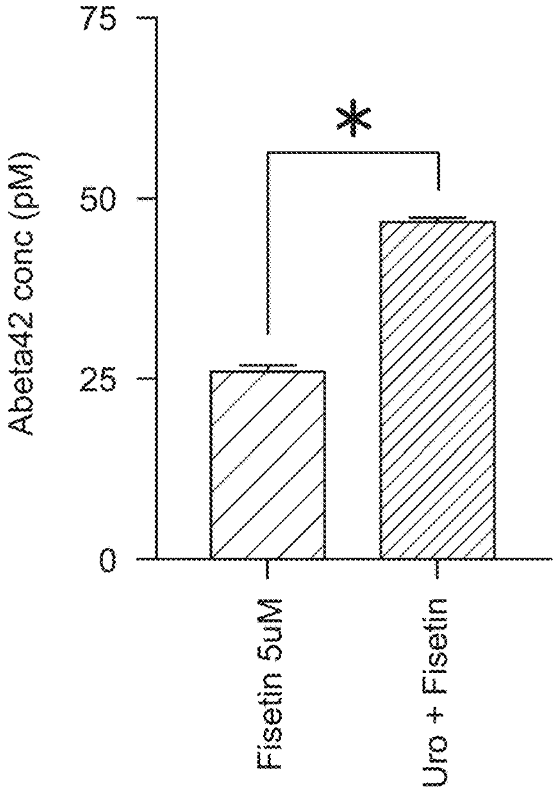
FIG. 3

COMPOSITIONS FOR TREATING NEURODEGENERATIVE DISEASES

CLAIM OF PRIORITY

This application is a continuation of U.S. patent application Ser. No. 19/153,936, filed Aug. 5, 2025, which is the U.S. National Phase Application under 35 U.S.C. § 371 of International Patent Application No. PCT/US2024/014677, filed Feb. 6, 2024, which claims the benefit of U.S. Provisional Patent Application Ser. No. 63/443,690, filed on Feb. 6, 2023 and U.S. Provisional Patent Application Ser. No. 63/512,012, filed on Jul. 5, 2023, the contents of each are hereby incorporated by reference in their entireties.

BACKGROUND

Neurodegenerative diseases of the central nervous system (CNS) cause progressive loss of neuronal structure and function and are devastating diseases for affected patients and their families. While various agents are known or have been suggested for treating neurodegenerative diseases, effective therapies are scarce or non-existent. Thus, there is need for improved approaches for treating neurodegenerative diseases.

SUMMARY

The present disclosure provides certain insights regarding, and technologies for, treatment and/or prevention of neurodegenerative diseases. Among other things, the present disclosure provides certain combinations of agents with unexpected and/or synergistic effects in treatment and/or prevention of neurodegenerative disease. The present disclosure also identifies the source of a problem with certain conventional or proposed strategies for treating and/or preventing neurodegenerative disease, for example in failing to appreciate importance and/or benefit of certain combination therapies.

The present disclosure specifically provides combinations of a urolithin A agent and a fisetin agent, and demonstrates surprising features of combination therapy with such a urolithin A agent and a fisetin agent in treating and/or preventing neurodegenerative disease. The present disclosure further documents usefulness of such urolithin A agent and fisetin agent combination therapy when further combined with additional agents.

In one aspect, provided herein are methods of treating or preventing a neurodegenerative disease in a subject in need thereof, the methods include administering to the subject a therapeutically effective amount of a urolithin A agent, and a therapeutically effective amount of a fisetin agent. In some embodiments, the present disclosure provides a method of reducing pathogenic microglial pro-inflammatory activation in a subject, the method comprising administering to the subject a therapeutically effective amount of a urolithin A agent, and a therapeutically effective amount of a fisetin agent. In some embodiments, the present disclosure provides a method of promoting microglial Aβ clearance in a subject, the method comprising administering to the subject a therapeutically effective amount of a urolithin A agent, and a therapeutically effective amount of a fisetin agent. In some embodiments, the present disclosure provides a method of reducing pathogenic microglial pro-inflammatory activation and promoting microglial Aβ clearance in a subject, the method comprising administering to the subject a therapeutically effective amount of a urolithin A agent, and a therapeutically effective amount of a fisetin agent.

In some embodiments, the present disclosure provides methods of treating, preventing, or decreasing neuroinflammation. In some embodiments, neuroinflammation can be caused by or associated with neurodegenerative disorders (e.g., those described herein), other diseases, disorders, and conditions, such as viral infection, autoimmune disorders, mental stress (e.g., stress caused from overworking, lack of sleep, and the like), metabolic disorders, and injury, or aging. In some embodiments, neuroinflammation is caused by or associated with a viral infection. In some embodiments, a viral infection is a SARS-CoV-2 infection. In some embodiments neuroinflammation is characterized by microglia activation in the subject.

In some embodiments, the present disclosure provides methods of treating or preventing a symptom or feature associated with a neurodegenerative disease. In some embodiments, a symptom or feature of a neurodegenerative disease is memory loss, cognitive decline, brain fog, increased Aβ plaque production and/or increased Aβ plaque levels.

In some embodiments, the present disclosure provides methods of treating or preventing brain fog. In some embodiments, brain fog is not associated with any particular clinical disease, disorder, or condition. In some embodiments, brain fog is associated with lack of sleep, stress, and the like. In some embodiments, the neurodegenerative disease is Alzheimer's disease, Parkinson's disease, Huntington's Disease, Amyotrophic Lateral Sclerosis, Multiple Sclerosis, a polyglutamine expansion disorder, a trinucleotide repeat expansion disorder, Alexander disease, Alpe's disease, ataxia telangiectasia, Batten disease, Canavan disease, Cockayne syndrome, corticobasal degeneration, Creutzfeldt-Jakob disease, ischemia stroke, Krabbe disease, Lewy body dementia, multiple system atrophy, Pelizaeus-Merzbacher disease, Pick's disease, primary lateral sclerosis, Refsum's disease, Sandhoff disease, Schilder's disease, spinal cord injury, spinal muscular atrophy, SteeleRichardson-Olszewski disease, or Tabes dorsalis. In some embodiments, the urolithin A agent and the fisetin agent are administered concurrently. In some embodiments, the urolithin A agent and the fisetin agent are administered separately. In some embodiments, the urolithin A agent and the fisetin agent are administered daily. In some embodiments, the urolithin A agent and the fisetin agent are administered once a day, twice a day, or three or more times a day. In some embodiments, the urolithin A agent is urolithin A. In some embodiments, the methods include administering urolithin A to the subject at a dose of about 1 mg to about 2500 mg. In some embodiment, urolithin A is administered to the subject in an amount of about 1 mg to about 1000 mg per day. In some embodiments, urolithin A is administered to the subject once per day. In some embodiments, the methods include administering urolithin A to the subject at a dose of about 300 mg to about 900 mg twice a day. In some embodiments, the fisetin agent is fisetin. In some embodiments, the methods include administering fisetin to the subject at a dose of about 0.5 mg to about 2500 mg. In some embodiments, fisetin is administered to the subject in an amount of about 1 mg to about 10 mg per day. In some embodiments, fisetin is administered to the subject once per day. In some embodiments, the methods include administering fisetin to the subject at a dose of about 1 mg to about 10 mg twice a day. In some embodiments, the methods include administering fisetin to the subject at a dose of about 2 mg to about 6 mg twice a day. In some embodiments, the subject has one or more symptoms associated with the neurodegenerative disease. In some embodiments, the subject is at risk for developing the neurodegenerative disease. In some embodiments, the methods further include, prior to administration, determining or having determined that the subject is at risk for developing the neurodegenerative disease. In some embodiments, the methods further include administering to the subject one or both of nicotinamide riboside or pharmaceutically acceptable salts thereof, and cat's claw extracts or components thereof.

In some embodiments, the methods include administering to the subject a therapeutically effective amount of a combination of a urolithin A agent and a fisetin agent. In some embodiments, the methods include administering to the subject a therapeutically effective amount of a combination of a urolithin A agent that is urolithin A and a fisetin agent that is fisetin. In some embodiments, the methods include administering to the subject a therapeutically effective amount of a combination of a urolithin A agent that is urolithin A and a fisetin agent that is quercetin. In some embodiments, urolithin A is administered in an amount that is about 1 to about 2500 mg per day. In some embodiments fisetin is administered in an amount that is about 1 to about 1000 mg per day. In some embodiments, quercetin is administered in an amount that is about 1 to about 1000 mg per day.

In some embodiments, the method further comprises administering to the subject nicotinamide riboside. In some embodiments, nicotinamide riboside is administered at an amount of about 1 mg to about 800 mg per day. In some embodiments, the methods further include administering to the subject quercetin. In some embodiments, quercetin is administered at an amount of about 1 mg to about 1000 mg. In some embodiments, the methods further include administering to the subject a cat's claw extract. In some embodiments, the cat's claw extract is administered at an amount of about 1 to about 1200 mg. In some embodiments, nicotinamide riboside is administered at an amount of about 100 mg to about 800 mg per day. In some embodiments, the methods further include administering to the subject quercetin. In some embodiments, quercetin is administered at an amount of about 50 mg to about 1000 mg. In some embodiments, the methods further include administering to the subject a cat's claw extract. In some embodiments, the cat's claw extract is administered at an amount of about 100 to about 1200 mg.

In some aspects, provided herein are methods of treating or preventing a neurodegenerative disease in a subject in need thereof, the methods include administering to the subject a therapeutically effective amount of an ellagitannin or ellagic acid, and a therapeutically effective amount of a fisetin agent. In some embodiments, the subject is a urolithin A producer. In some embodiments, the methods further include, prior to administration, determining or having determined that the subject is a urolithin A producer. In some embodiments, the methods include detecting or having detected one or more bacterial species associated with urolithin A production in a biological sample of the subject. In some embodiments, the bacterial species is *Gordonibacter urolithinfaciens* or *Ellagibacter isourolithinifaciens*. In some embodiments, the neurodegenerative disease is Alzheimer's disease, Parkinson's disease, Huntington's Disease, Amyotrophic Lateral Sclerosis, Multiple Sclerosis, a polyglutamine expansion disorder, a trinucleotide repeat expansion disorder, Alexander disease, Alpe's disease, ataxia telangiectasia, Batten disease, Canavan disease, Cockayne syndrome, corticobasal degeneration, Creutzfeldt-Jakob disease, ischemia stroke, Krabbe disease, Lewy body dementia, multiple system atrophy, Pelizaeus-Merzbacher disease, Pick's disease, primary lateral sclerosis, Refsum's disease, Sandhoff disease, Schilder's disease, spinal cord injury, spinal muscular atrophy, SteeleRichardson-Olszewski disease, or Tabes dorsalis. In some embodiments, the ellagitannin or ellagic acid and the fisetin agent are administered concurrently. In some embodiments, the ellagitannin or ellagic acid and the fisetin agent are administered separately. In some embodiments, the ellagitannin or ellagic acid and the fisetin agent are administered daily. In some embodiments, the ellagitannin or ellagic acid and the fisetin agent are administered once a day, twice a day, or three or more times a day. In some embodiments, the fisetin agent is fisetin. In some embodiments, the methods include administering fisetin to the subject at a dose of about 0.5 mg to about 2500 mg. In some embodiments, fisetin is administered to the subject in an amount of about 1 mg to about 10 mg per day. In some embodiments, fisetin is administered to the subject once per day. In some embodiments, the method comprises administering fisetin to the subject at a dose of about 1 mg to about 10 mg twice a day. In some embodiments, the methods include administering fisetin to the subject at a dose of about 2 mg to about 6 mg twice a day. In some embodiments, the fisetin agent is quercetin. In some embodiments, the methods include administering quercetin to the subject at a dose of about 0.5 mg to about 2500 mg. In some embodiments, quercetin is administered to the subject in an amount of about 1 mg to about 10 mg per day. In some embodiments, quercetin is administered to the subject once per day. In some embodiments, the method comprises administering quercetin to the subject at a dose of about 1 mg to about 10 mg twice a day. In some embodiments, the methods include administering quercetin to the subject at a dose of about 2 mg to about 6 mg twice a day. In some embodiments, the subject has one or more symptoms associated with the neurodegenerative disease. In some embodiments, the subject is at risk for developing the neurodegenerative disease. In some embodiments, the methods further include, prior to administration, determining or having determined that the subject has one or more symptoms associated with the neurodegenerative disease. In some embodiments, the methods further include, prior to administration, determining or having determined that the subject is at risk for developing the neurodegenerative disease. In some embodiments, the methods further include administering to the subject one or both of nicotinamide riboside or pharmaceutically acceptable salts thereof, and cat's claw extracts or components thereof.

In some embodiments, the methods include administering to the subject a therapeutically effective amount of a combination of an ellagitannin or ellagic acid and fisetin. In some embodiments, the methods further include administering to the subject nicotinamide riboside. In some embodiments, nicotinamide riboside is administered at an amount of about 100 mg to about 800 mg per day. In some embodiments, the methods further include administering to the subject quercetin. In some embodiments, quercetin is administered at an amount of about 50 mg to about 1000 mg. In some embodiments, the methods further include administering to the subject a cat's claw extract. In some embodiments, cat's claw extract is administered at an amount of about 100 to about 1200 mg.

In some aspects, provided herein are methods of treating or preventing a neurodegenerative disease in a subject in need thereof, the methods include administering to the subject a therapeutically effective amount of an ellagitannin or ellagic acid, a therapeutically effective amount of a fisetin agent, and a composition comprising one or more bacterial species associated with urolithin A production. In some embodiments, the bacterial species is *Gordonibacter urolithinfaciens* or *Ellagibacter isourolithinifaciens*. In some embodiments, the neurodegenerative disease is Alzheimer's disease, Parkinson's disease, Huntington's Disease, Amyotrophic Lateral Sclerosis, Multiple Sclerosis, a polyglutamine expansion disorder, a trinucleotide repeat expansion disorder, Alexander disease, Alpe's disease, ataxia telangiectasia, Batten disease, Canavan disease, Cockayne syndrome, corticobasal degeneration, Creutzfeldt-Jakob disease, ischemia stroke, Krabbe disease, Lewy body dementia, multiple system atrophy, Pelizaeus-Merzbacher disease, Pick's disease, primary lateral sclerosis, Refsum's disease, Sandhoff disease, Schilder's disease, spinal cord injury, spinal muscular atrophy, SteeleRichardson-Olszewski disease, or Tabes dorsalis. In some embodiments, the ellagitannin or ellagic acid, the fisetin agent, and the composition comprising one or more bacterial species are administered concurrently. In some embodiments, the ellagitannin or ellagic acid, the fisetin agent, and the composition comprising one or more bacterial species are administered separately. In some embodiments, the ellagitannin or ellagic acid and the fisetin agent are administered daily. In some embodiments, the ellagitannin or ellagic acid and the fisetin agent are administered once a day, twice a day, or three or more times a day. In some embodiments, the fisetin agent is fisetin. In some embodiments, the methods include administering fisetin to the subject at a dose of about 0.5 mg to about 2500 mg. In some embodiments, fisetin is administered to the subject in an amount of about 1 mg to about 10 mg per day. In some embodiments, fisetin is administered to the subject once per day. In some embodiments, the methods include administering fisetin to the subject at a dose of about 1 mg to about 10 mg twice a day. In some embodiments, the methods include administering fisetin to the subject at a dose of about 2 mg to about 6 mg twice a day. In some embodiments, the subject has one or more symptoms associated with the neurodegenerative disease. In some embodiments, the subject is at risk for developing the neurodegenerative disease. In some embodiments, the methods further include, prior to administration, determining or having determined that the subject has one or more symptoms associated with the neurodegenerative disease. In some embodiments, the methods further include, prior to administration, determining or having determined that the subject is at risk for developing the neurodegenerative disease. In some embodiments, the methods further include administering to the subject one or more agents selected from nicotinamide riboside or pharmaceutically acceptable salts thereof, or cat's claw extracts or components thereof. In some embodiments, the methods include administering to the subject a therapeutically effective amount of a combination of an ellagitannin or ellagic acid, fisetin, and a composition comprising one or more bacterial species associated with urolithin A production. In some embodiments, the methods further include administering to the subject nicotinamide riboside. In some embodiments, nicotinamide riboside is administered at an amount of about 100 mg to about 800 mg per day. In some embodiments, the methods further include administering to the subject quercetin. In some embodiments, quercetin is administered at an amount of about 50 mg to about 1000 mg. In some embodiments, the methods further include administering to the subject a cat's claw extract. In some embodiments, cat's claw extract is administered at an amount of about 100 to about 1200 mg.

Also provided herein are combinations of one or more agents as disclosed herein for treating or preventing a neurodegenerative disease in a subject in need thereof, including e.g., urolithin A agents, fisetin agents, nicotinamide riboside or pharmaceutically acceptable salts thereof, and cat's claw extracts or components thereof.

Unless otherwise defined, all technical and scientific terms used herein have the same meaning as commonly understood by one of ordinary skill in the art to which the invention belongs. The methods and materials described herein are exemplary, and methods and materials similar or equivalent to those described herein can be used in the practice or testing of the present invention. All publications, patent applications, patents, and other references mentioned herein are incorporated by reference in their entirety. In case of conflict, the present application, including definitions, will control. The materials, methods, and examples are illustrative only and not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

The term "alkyl", used alone or as part of a larger moiety, refers to a saturated, optionally substituted straight or branched chain hydrocarbon group having (unless otherwise specified) 1-12, 1-10, 1-8, 1-6, 1-4, 1-3, or 1-2 carbon atoms (e.g., $C_{1-12}$, $C_{1-10}$, $C_{1-8}$, $C_{1-6}$, $C_{1-4}$, $C_{1-3}$, or $C_{1-2}$). Exemplary alkyl groups include methyl, ethyl, propyl, butyl, pentyl, hexyl, and heptyl.

The term "alkenyl", used alone or as part of a larger moiety, refers to an optionally substituted straight or branched chain or cyclic hydrocarbon group having at least one double bond and having (unless otherwise specified) 2-12, 2-10, 2-8, 2-6, 2-4, or 2-3 carbon atoms (e.g., $C_{2-12}$, $C_{2-10}$, $C_{2-8}$, $C_{2-6}$, $C_{2-4}$, or $C_{2-3}$). Exemplary alkenyl groups include ethenyl, propenyl, butenyl, pentenyl, hexenyl, and heptenyl. The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl, and cycloheptenyl.

The term "alkoxy" refers to the group-O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy.

The term “aryl” refers to an optionally substituted monocyclic and bicyclic ring systems having a total of six to fourteen ring members (e.g., $C_6$-$C_{14}$), wherein at least one ring in the system is aromatic and wherein each ring in the system contains three to seven ring members.

In some embodiments, an “aryl” group contains between six and twelve total ring members (e.g., $C_6$-$C_{12}$). The term “aryl” may be used interchangeably with the term “aryl ring”. In certain embodiments, “aryl” refers to an aromatic ring system which includes, but not limited to, phenyl, biphenyl, naphthyl, anthracyl and the like, which may bear one or more substituents. Unless otherwise specified, “aryl” groups are hydrocarbons. In some embodiments, an “aryl” ring system is an aromatic ring (e.g., phenyl) that is fused to a non-aromatic ring (e.g., cycloalkyl). Examples of aryl rings include that are fused include

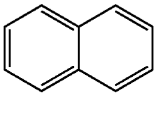,
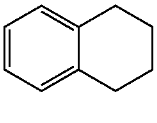, and
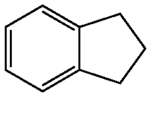.

As used herein, the term “cycloalkyl” refers to an optionally substituted saturated ring monocyclic or polycyclic system of about 3 to about 10 ring carbon atoms. Exemplary monocyclic cycloalkyl rings include cyclopropyl, cyclobutyl, cyclopentyl, cyclohexyl, and cycloheptyl.

The term “halogen” or “halo” means F, Cl, Br, or I.

Other features and advantages of the invention will be apparent from the following detailed description and from the claims.

BRIEF DESCRIPTION OF THE DRAWINGS

FIGS. 2A and 2B are graphs demonstrating the dose-response decrease of TNFα by urolithin A and fisetin, respectively. FIG. 2A is a graph showing the dose-response decrease of TNFα by urolithin A. FIG. 2B is a graph showing the dose-response decrease of TNFα by fisetin.

FIG. 3 shows microglial Aβ42 uptake/clearance in response to co-treatment with urolithin A and fisetin, as compared to fisetin alone.

FIG. 4A shows toxicity as measured using an LDL assay. FIG. 4B shows TNFα levels as measured by ELISA.

DETAILED DESCRIPTION

Figure 1:
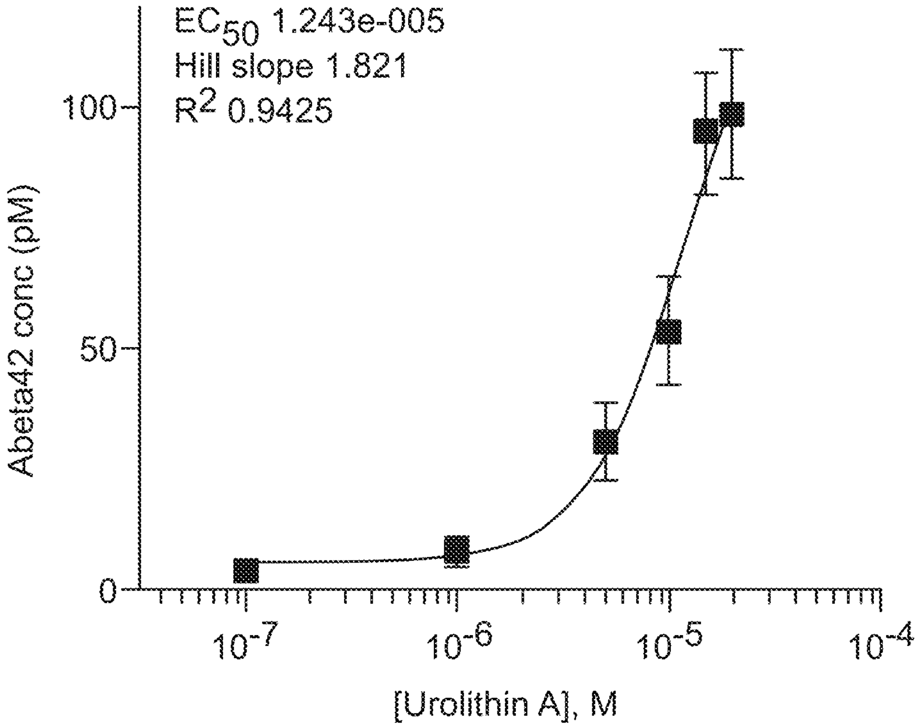
FIG. 1 is a graph demonstrating the dose-response increase in Aβ42 uptake by Urolithin A in microglial BV2 cells, measured by Aβ ELISA.

Neurodegenerative diseases occur when nerve cells in the brain or peripheral nervous system lose function over time and ultimately die. Although there are several medicines currently approved for managing neurodegenerative diseases, a large majority of them only help with associated symptoms. Neurodegenerative diseases such as Alzheimer's disease and dementia continue to be a clinical concern in most older people.

Amyloid beta (Aβ) plaque accumulation is considered one of the key drivers of Alzheimer's disease pathophysiology. Aβ elimination can be triggered by selectively activating microglia-mediated Aβ clearance. However, chronic and excessive reactive microgliosis (a process of expansion and activation of microglia) can also be detrimental in brain disorders such as Alzheimer's disease. For example, reactive microglia secrete pro-inflammatory cytokines, which induce astrogliosis, and contribute to brain cell death during late stages of Alzheimer's disease. Common anti-inflammatory drugs have been tested in Alzheimer's disease patients, but their efficacy in reducing reactive microgliosis has not been proven.

Applicant has discovered that the combination of a urolithin A agent and a fisetin agent demonstrate a synergistic effect in treating or preventing neurodegenerative diseases in subjects in need thereof. Surprisingly, Applicant has discovered that the combination of a urolithin A agent and a fisetin agent can concomitantly promote microglial Aβ clearance and reduce pathogenic microglial pro-inflammatory activation. Described combination therapy solves problems associated with previous therapies (in particular the failure to achieve both promotion of microglial Aβ clearance and reduction of pathogenic microglial pro-inflammatory activation). Applicant has also discovered that nicotinamide riboside, quercetin and cat's claw extracts have beneficial effects in promoting microglial Aβ clearance and reduce pathogenic microglial pro-inflammatory activation.

Applicant has surprisingly discovered that, while each of urolithin A agent or a fisetin agent may provide some benefit in isolation for promoting microglial Aβ clearance or reducing pathogenic microglial pro-inflammatory activation, when the two agents are combined, both of these effects are promoted in a manner that is more than simply additive. The effect of promoting microglial Aβ clearance can be illustrated through the measurement of Aβ concentration in particular assays, such as those described in Examples 1 and 2. Further, the effect of reducing pathogenic microglial pro-inflammatory activation can be illustrated through the measurement of TNFα concentration in particular assays, such as those described in Examples 1 and 2. As illustrated in these Examples, when comparing the impact of a urolithin A agent or a fisetin agent on one or both of promoting microglial Aβ clearance or reducing pathogenic microglial pro-inflammatory activation, Applicant has demonstrated that this combination of agents is surprisingly synergistic, having an effect that is more than simply additive.

Without wishing to be bound by theory, it is understood that this synergistic effect of a urolithin A agent and a fisetin agent, when used in combination to promote microglial Aβ clearance and reduce pathogenic microglial pro-inflammatory activation, is useful for the treatment of neurodegenerative disorders, and in particular achieve beneficial effects where other treatments to date have failed.

Accordingly, the present disclosure provides methods of treating or preventing (e.g., treating) neurodegenerative diseases comprising administering to the subject a urolithin A agent in combination with a fisetin agent.

In some embodiments, the present disclosure provides methods of treating or preventing a symptom or feature associated with a neurodegenerative disease. In some embodiments, a symptom or feature of a neurodegenerative disease is memory loss, cognitive decline, brain fog, increased Aβ plaque production and/or increased Aβ plaque levels. In some embodiments, a symptom or feature of a neurodegenerative disease is memory loss. In some embodiments, a symptom or feature of a neurodegenerative disease is brain fog. In some embodiments, a symptom or feature of a neurodegenerative disease is increased Aβ plaque production. In some embodiments, a symptom or feature of a neurodegenerative disease is increased Aβ plaque levels.

In some embodiments, the present disclosure provides methods of treating or preventing brain fog. In some embodiments, brain fog is not associated with any particular clinical disease, disorder, or condition. In some embodiments, brain fog is associated with lack of sleep, stress, and the like. Without wishing to be bound by any particular theory, the present disclosure proposes that provided combination(s) (e.g., that comprise and/or deliver a urolithin A agent and a fisetin agent, and optionally one or more additional agents), may be particularly useful and/or effective to alleviate or improve brain fog. As described herein, brain fog can refer to confusion, forgetfulness, lack of focus, lack of mental clarity, and the like.

In some embodiments, the present disclosure provides methods of treating, preventing, or decreasing neuroinflammation. In some embodiments, neuroinflammation can be caused by or associated with neurodegenerative disorders (e.g., those described herein), other diseases, disorders, and conditions, such as viral infection, autoimmune disorders, mental stress (e.g., stress caused from overworking, lack of sleep, and the like), metabolic disorders, and injury, or aging. In some embodiments, neuroinflammation is caused by or associated with a viral infection. In some embodiments, a viral infection is a SARS-CoV-2 infection. In some embodiments neuroinflammation is characterized by microglia activation in the subject. In some embodiments, the present disclosure provides a method of treating, preventing, or decreasing neuroinflammation in a subject comprising administering to the subject a urolithin A agent and a fisetin agent. In some embodiments, the present disclosure provides a method of treating, preventing, or decreasing neuroinflammation in a subject comprising administering to the subject a urolithin A agent and a fisetin agent in combination with one or more additional components described herein.

Also contemplated herein are methods of treating or preventing (e.g., treating) neurodegenerative diseases in a subject in need thereof, comprising administering to the subject a urolithin A precursor, e.g., ellagitannin or ellagic acid in combination with a fisetin agent, wherein the method can further include determining or having determined that the subject is capable of metabolizing ellagitannin or ellagic acid into urolithin A.

Also provided herein are methods of treating or preventing (e.g., treating) neurodegenerative diseases in a subject in need thereof, comprising administering to the subject an ellagitannin or ellagic acid, in combination with a fisetin agent, and one or more bacterial species that are associated with urolithin A production.

Urolithin A Agents

Urolithin A agents can be utilized for the treating or preventing (e.g., treating) of neurodegenerative diseases as disclosed herein.

In certain embodiments, the urolithin A agents have a structure of Formula I:

Formula I

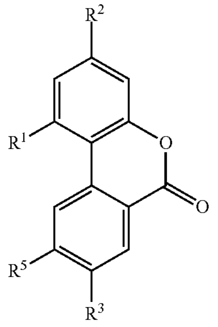

or a pharmaceutically acceptable salt thereof, wherein $R^1$ is —H, —OH, or —$OR^4$;

$R^2$ is —H, —OH, —$OR^4$, —$NH_2$, —$NHR^4$, —SH, —$SR^4$, —F, —Cl, —Br, —CN, —OCN, —$O(CH_2)_n NH_2$, —$O(CH_2)_nCH_3$, —$C_1$ to $C_{10}$ alkyl, $C_3$-$C_6$ cycloalkyl, —$C_6$ to $C_{12}$ aryl, —$SOCH_3$, —$SO_2$, —$ONO_2$, —$NO_2$, and —$N_3$;

$R^3$ is —H, —OH, or —$OR^4$;

$R^5$ is —H or —$OR^4$;

$R^4$ is a $C_1$ to $C_{10}$ alkyl;

n is from 1 to 10, wherein each alkyl, cycloalkyl, and aryl of $R^2$ is optionally substituted with one or more substituents selected from halogen, $C_1$ to $C_{10}$ alkyl, $C_3$ to $C_6$ cycloalkyl, and $C_6$ to $C_{12}$ aryl.

In some embodiments of Formula I, one instance of $R^2$ is —OH, another instance of $R^2$ is —H, $R^1$ is —H, and $R^3$ is —OH.

In some embodiments, the urolithin A agent is urolithin A, or a pharmaceutically acceptable salt thereof.

Urolithin A (3,8-dihydroxy-6H-benzo[b,d]pyran-6-one) is produced, e.g., as a metabolite resulting from the transformation of ellagitannins by the gut bacterial. Ellagitannins are hydrolyzed in the gut to release ellagic acid, which in turn, is further processed by the gut microflora into urolithins. Urolithin A has the following structure:

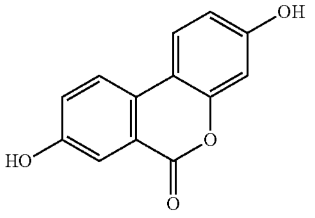 [SMILES: O=c1oc2cc(O)ccc2c2ccc(O)cc12]

Urolithin A is commercially available (see, e.g., Sigma-Aldrich, SML1791) and can also be obtained by methods known to the skilled artisan.

In certain embodiments, urolithin A is obtained from natural sources, including, for example, nuts, berries and pomegranate using conventional isolation methods.

In other embodiments, urolithin A is synthesized using conventional organic synthesis methods. For example, urolithin A can be prepared by combining in an alkaline aqueous solution the following starting materials and reagents: a copper-containing catalyst, 2-bromo-5-hydroxybenzoic acid, and resorcinol, which produces the salt of urolithin A, followed by protonating such salt of urolithin A to yield urolithin A. (See, e.g. WO2019168972).

In certain embodiments, the urolithin A agent has a structure of formula Ia:

Formula Ia

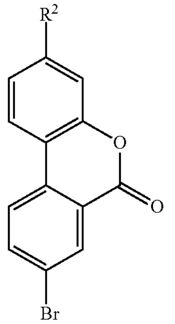

or a pharmaceutically acceptable salt thereof, wherein $R^2$ is selected from —H, —OH, —$OR^4$, —$NH_2$, —$NHR^4$, —SH, —$SR^4$, —F, —Cl, —Br, —CN, —OCN, —$O(CH_2)_nNH_2$, —$O(CH_2)_nCH_3$, —$C_1$ to $C_{10}$ alkyl, $C_3$-$C_6$ cycloalkyl, —$C_6$ to $C_{12}$ aryl, —$SOCH_3$, —$SO_2$, —$ONO_2$, —$NO_2$, and —$N_3$;

$R^3$ is OH or $OR^4$;

$R^4$ is R $C_1$ to $C_{10}$ alkyl;

n is from 1 to 10; and wherein each alkyl, cycloalkyl, and aryl of $R^2$ is optionally substituted with one or more substituents selected from halogen, $C_1$ to $C_{10}$ alkyl, $C_3$ to $C_6$ cycloalkyl, and $C_6$ to $C_{12}$ aryl.

In some embodiments, a urolithin A agent is one described in US 2009/0326057 A1, which is incorporated herein by reference in its entirety.

In certain embodiments of the compound of Formula I, or a pharmaceutically acceptable salt thereof, $R^1$ is —H, —OH, or —$OCH_3$;

$R^2$ is —OH or —$OCH_3$;

$R^3$ is —H, —OH, or —$OCH_3$; and $R^5$ is —H or —$OCH_3$.

In certain embodiments of the compound of Formula I, or a pharmaceutically acceptable salt thereof, $R^1$ is —H, $R^2$ is —OH, $R^3$ is —H, and $R^5$ is —H.

In certain embodiments of the compound of Formula I, or a pharmaceutically acceptable salt thereof, $R^1$ is —H, $R^2$ is —$OCH_3$, $R^3$ is —H, and $R^5$ is —H.

In certain embodiments of the compound of Formula I, or a pharmaceutically acceptable salt thereof, $R^1$ is —OH, $R^2$ is —OH, $R^3$ is —H, and $R^5$ is —H.

In certain embodiments of the compound of Formula I, or a pharmaceutically acceptable salt thereof, $R^1$ is —$OCH_3$, $R^2$ is —$OCH_3$, $R^3$ is —H, and $R^5$ is —H.

In certain embodiments of the compound of Formula I, or a pharmaceutically acceptable salt thereof, $R^1$ is —H, $R^2$ is —OH, $R^3$ is —OH, and $R^5$ is —H.

In certain embodiments of the compound of Formula I, or a pharmaceutically acceptable salt thereof, $R^1$ is —H, $R^2$ is —$OCH_3$, $R^3$ is —$OCH_3$, and $R^5$ is —H.

In certain embodiments of the compound of Formula I, or a pharmaceutically acceptable salt thereof, $R^1$ is —OH, $R^2$ is —OH, $R^3$ is —$OCH_3$, and $R^5$ is —$OCH_3$.

In certain embodiments of the compound of Formula I, or a pharmaceutically acceptable salt thereof, $R^1$ is —H, $R^2$ is —OH, $R^3$ is —$OCH_3$, and $R^5$ is —H.

In certain embodiments of the compound of Formula I, or a pharmaceutically acceptable salt thereof, $R^1$ is —OH, $R^2$ is —OH, $R^3$ is —OH, and $R^5$ is —H.

In certain embodiments of the compound of Formula I, or a pharmaceutically acceptable salt thereof, $R^1$ is —$OCH_3$, $R^2$ is —$OCH_3$, $R^3$ is —$OCH_3$, and $R^5$ is —H.

In certain embodiments of the compound of Formula I, or a pharmaceutically acceptable salt thereof, $R^1$ is —H, $R^2$ is —OH, $R^3$ is —$OCH_3$, and $R^5$ is —$OCH_3$.

In certain embodiments of the compound of Formula I, or a pharmaceutically acceptable salt thereof, $R^1$ is —OH, $R^2$ is —OH, $R^3$ is —$OCH_3$, and $R^5$ is —H.

In some embodiments, a urolithin A agent is one described in Noshadi, B., et al., *Chem. Biodiversity* 2020, 17, e2000197, which is incorporated herein by reference in its entirety.

In some embodiments, urolithin A agents include, but are not limited to: (8-Hydroxy-6-oxo-6H-benzo[c]chromen-3-yl (tert butoxycarbonyl) tryptophanate) with the structure

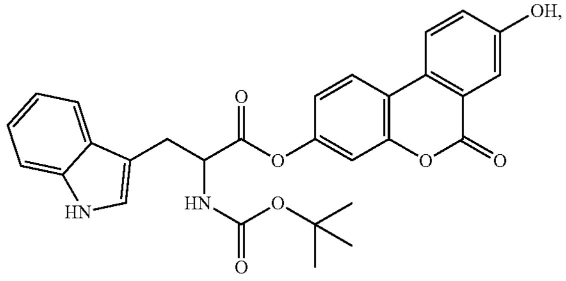 [SMILES: CC(C)(C)OC(=O)NC(Cc1c[nH]c2ccccc12)C(=O)Oc1ccc2c(c1)oc(=O)c1cc(O)ccc12]

6H-benzo[c]chromene-3,8-diol with the structure

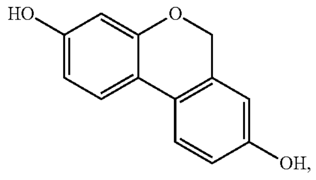 [SMILES: Oc1ccc2c(c1)COc1cc(O)ccc1-2]

3-Hydroxy-6H-benzo[c]chromen-6-one (=3-Hydroxy-6H-dibenzo[b,d]pyran-6-one, 3-Methoxy-6H-benzo[c]chromen-6-one(=3-Methoxy-6H-dibenzo[b,d]pyran-6-one, 1,3-Dihydroxy-6H-benzo[c]chromen-6-one(=1,3-Dihydroxy-6H-dibenzo[b,d]pyran-6-one, 1,3-Dimethoxy-6H-benzo[c]chromen-6-one(=1,3-Dimethoxy-6H-dibenzo[b,d]pyran-6-one, 3,8-Dimethoxy-6H-benzo[c]chromen-6-one (=3,8-Dimethoxy-6H-dibenzo[b,d]pyran-6-one, 1,3-Dihydroxy-8,9-dimethoxy-6H-benzo[c]chromen-6-one(=1,3-Dihydroxy-8,9-dimethoxy-6H-dibenzo[b,d]pyran-6-one, 3-Hydroxy-8-methoxy-6H-benzo[c]chromen-6-one(=3-Hydroxy-8-methoxy-6H-dibenzo[b,d]pyran-6-one, 1,3,8-Trihydroxy-6H-benzo[c]chromen-6-one (=1,3,8-Trihydroxy-6H-dibenzo[b,d]pyran-6-one, 1,3,8-Trimethoxy-6H-benzo[c]chromen-6-one (=1,3,8-Trimethoxy-6H-dibenzo[b,d]pyran-6-one, 3-Hydroxy-8,9-dimethoxy-6H-benzo[c]chromen-6-one (=3-Hydroxy-8,9-dimethoxy-6H-dibenzo[b,d]pyran-6-one, 1,3-Dihydroxy-8-methoxy-6H-benzo[c]chromen-6-one(=1,3-Dihydroxy-8-methoxy-6H-dibenzo[b,d]pyran-6-one, urolithin A-glucuronide, urolithin A-sulfate, and urolithin A-aglycone, and methylated urolithin A.

In some embodiments, urolithin A precursors, or analogs or metabolites thereof, may be utilized in accordance with the present disclosure. In some embodiments, the present disclosure encompasses methods of delivering a urolithin A agent to a subject via a precursor, analog, or metabolite. As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete way(s). In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

In certain embodiments, the precursor of urolithin A include ellagitannins and ellagic acid. In some embodiments, an analog or metabolite of an ellagitannin or ellagic acid, may be useful in accordance with the present disclosure. Those skilled in the art will be aware of a variety of analogs or metabolites of ellagitannins or ellagic acid. Ellagitannins useful for the present disclosure can include monomeric ellagitannins, C-glycosidic ellagitannins with an open-chain glucose core, condensates of C-glycosidic tannins with flavan-3-ol (complex tannin), and oligomers which are produced through intermolecular C—O or C—C bonds between monomers. Exemplary ellagitannins include punicalagin, sanguiin H6, lambertianin C, pedunculagin, vescalagin, castalagin, casuarictin and potentillin.

In certain embodiments, one or more urolithin A precursors, e.g., ellagitannins or ellagic acid, or their analogs and metabolites are administered to urolithin A producers, which are individuals that are capable of metabolizing ellagitannins or ellagic acid into urolithin A. For example, some individuals are able to produce urolithin A via their gut bacteria while others can also produce Isourolithin A and urolithin B. Bacterial species that are associated with urolithin A production are known in the art. For example, bacterial species belonging to the Clostridiales and Ruminococcaceae family, and *Gordonibacter urolithinfaciens, Ellagibacter isourolithinifaciens*, and *Akkermansia muciniphilia* have been known to show increased abundance in urolithin A producers. Accordingly, the present disclosure also provides methods comprising administering ellagitannins and/or ellagic acid to a subject where the methods can further include determining or having determined that the subject is a urolithin A producer. Subjects can be determined to be urolithin A producers via analysis of their gut microbiota through blood, urine or fecal samples and detection of one or more bacterial species associated with urolithin A production.

Fisetin Agents

Fisetin agents can be utilized for the treating or preventing (e.g., treating) of neurodegenerative diseases as disclosed herein.

In certain embodiments, the fisetin agent has a structure of Formula II:

Formula II

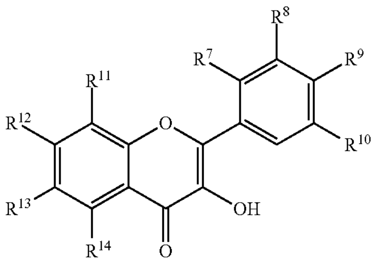

or a pharmaceutically acceptable salt thereof,
wherein
$R^7$ is H, $CF_3$, $OCH_3$, Cl, Br;
$R^8$ is H, $CF_3$, OH, $OCH_3$, F, Cl, Br, or t-Bu;
$R^9$ is H, $CF_3$, Cl, Br, OH, $C_1$ to $C_6$ alkoxy, $C_3$ to $C_6$ cycloalkyl, $C_1$ to $C_6$ alkyl, or $SCF_3$;
$R^{10}$ is H, $CF_3$, $C_1$ to $C_6$ alkoxy, $C_3$ to $C_6$ cycloalkyl, or $C_1$ to $C_6$ alkyl;
$R^{11}$ is H or $NO_2$;
$R^{12}$ is H, $CH_3$, OH, $OCH_3$, Cl or Br;
$R^{13}$ is H, $CH_3$, F, Cl or Br; and
$R^{14}$ is H or OH.

In certain embodiments of the compound of Formula II, or a pharmaceutically acceptable salt thereof,
$R^7$ is H, $CF_3$, $OCH_3$, Cl, Br;
$R^8$ is H, $CF_3$, OH, $OCH_3$, F, Cl, Br, or t-Bu;
$R^9$ is H, $CF_3$, Cl, Br, OH, $C_1$ to $C_6$ alkoxy, $C_3$ to $C_6$ cycloalkyl, $C_1$ to $C_6$ alkyl, or $SCF_3$;
$R^{10}$ is H, $CF_3$, $C_1$ to $C_6$ alkoxy, $C_3$ to $C_6$ cycloalkyl, or $C_1$ to $C_6$ alkyl;
$R^{11}$ is H or $NO_2$;
$R^{12}$ is H, $CH_3$, OH, $OCH_3$, Cl or Br;
$R^{13}$ is H, $CH_3$, F, Cl or Br; and
$R^{14}$ is H or OH.

In some embodiments, the fisetin agent is fisetin, or a pharmaceutically acceptable salt thereof.

Fisetin (3,3',4',7-tetrahydroxyflavone) is a plant flavonol from the flavonoid group of polyphenols and has the following structure:

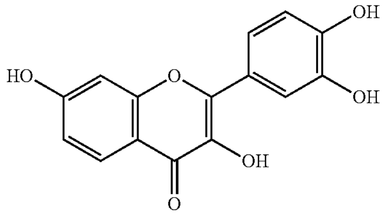 [SMILES: O=c1c(O)c(-c2ccc(O)c(O)c2)oc2cc(O)ccc12]

Fisetin is commercially available (see, e.g., Sigma-Aldrich, PHL82542) and can be obtained by methods known to the skilled artisan.

In certain embodiments, fisetin is obtained from natural sources, including from fruits and vegetables, such as strawberry, apple, persimmon, grape, onion and cucumber.

In other embodiments, fisetin is synthesized using conventional organic synthesis methods. For example, fisetin can be prepared using methods described in Grynkiewicz and Demchuk, New Perspectives for Fisetin, Front. Chem. 7:697 (2019).

In some embodiments, the fisetin agent is quercetin, or a pharmaceutically acceptable salt thereof.

Quercetin (3,3',4',5,7-pentahydroxyflavone) is an antioxidant flavonoid and has the following structure:

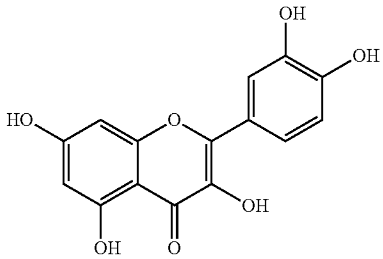 [SMILES: O=c1c(O)c(-c2ccc(O)c(O)c2)oc2cc(O)cc(O)c12]

Quercetin is commercially available and can be obtained by methods known to the skilled artisan.

In certain embodiments, quercetin is obtained from natural sources, including from fruits and vegetables, such as apples, onions, grapes, berries, cherries, broccoli, and citrus fruits.

In certain embodiments, the fisetin agent has a structure of Formula IIa:

Formula IIa

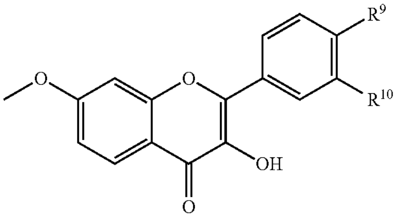

wherein $R^9$ is H, $C_1$ to $C_6$ alkoxy, or $C_3$ to $C_6$ cycloalkyl $R^{10}$ is H, $C_1$ to $C_6$ alkoxy, or $C_3$ to $C_6$ cycloalkyl.

In some embodiments, a urolithin A agent is one described in U.S. Pat. No. 11,591,305B2, which is incorporated herein by reference in its entirety.

In certain embodiments, the fisetin agent is a glucuronide conjugate of fisetin or 3'-methoxylated metabolite of fisetin (e.g. geraldol).

In certain embodiments, the fisetin agent has a structure of Formula IIb:

Formula IIb

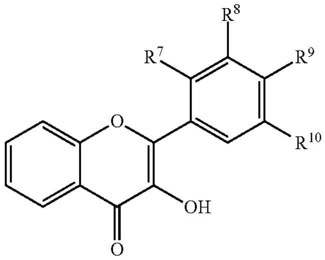

or a pharmaceutically acceptable salt thereof.

In certain embodiments of the compound of Formula IIb, or a pharmaceutically acceptable salt thereof, $R^7$ is H, $R^8$ is H, $R^9$ is H, and $R^{10}$ is H.

In certain embodiments of the compound of Formula IIb, or a pharmaceutically acceptable salt thereof, $R^7$ is H, $R^8$ is $OCH_3$, $R^9$ is H, and $R^{10}$ is H.

In certain embodiments of the compound of Formula IIb, or a pharmaceutically acceptable salt thereof, $R^7$ is H, $R^8$ is H, $R^9$ is $SCF_3$, and $R^{10}$ is H.

In certain embodiments of the compound of Formula IIb, or a pharmaceutically acceptable salt thereof, $R^7$ is Cl, $R^8$ is H, $R^9$ is Br, and $R^{10}$ is H.

In certain embodiments of the compound of Formula IIb, or a pharmaceutically acceptable salt thereof, $R^7$ is $CF_3$, $R^8$ is H, $R^9$ is $CF_3$, and $R^{10}$ is H.

In certain embodiments of the compound of Formula IIb, or a pharmaceutically acceptable salt thereof, $R^7$ is H, $R^8$ is $CF_3$, $R^9$ is H, and $R^{10}$ is $CF_3$.

In certain embodiments of the compound of Formula IIb, or a pharmaceutically acceptable salt thereof, $R^7$ is H, $R^8$ is H, $R^9$ is OBn, and $R^{10}$ is H.

In certain embodiments of the compound of Formula IIb, or a pharmaceutically acceptable salt thereof, $R^7$ is $OCH_3$, $R^8$ is H, $R^9$ is $OCH_3$, and $R^{10}$ is $OCH_3$.

In certain embodiments, the fisetin agent has a structure of Formula IIc:

Formula IIc

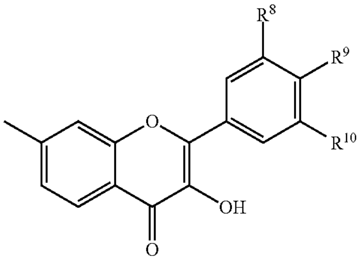

or a pharmaceutically acceptable salt thereof.

In certain embodiments of the compound of Formula IIc, or a pharmaceutically acceptable salt thereof, $R^8$ is H, $R^9$ is Cl, and $R^{10}$ is H.

In certain embodiments of the compound of Formula IIc, or a pharmaceutically acceptable salt thereof, $R^8$ is H, $R^9$ is $OCH_3$, and $R^{10}$ is H.

In certain embodiments of the compound of Formula IIc, or a pharmaceutically acceptable salt thereof, $R^8$ is Br, $R^9$ is $OCH_3$, and $R^{10}$ is $OCH_3$.

In certain embodiments of the compound of Formula IIc, or a pharmaceutically acceptable salt thereof, $R^8$ is H, $R^9$ is H, and $R^{10}$ is t-Bu.

In certain embodiments, the fisetin agent has a structure of Formula IId:

Formula IId

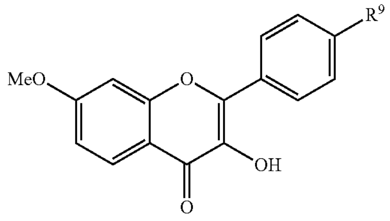

or a pharmaceutically acceptable salt thereof.

In certain embodiments of the compound of Formula IIc, or a pharmaceutically acceptable salt thereof, $R^9$ is Br.

In certain embodiments of the compound of Formula IIc, or a pharmaceutically acceptable salt thereof, $R^9$ is t-Bu.

In certain embodiments, the fisetin agent has a structure of Formula IIe:

Formula IIe

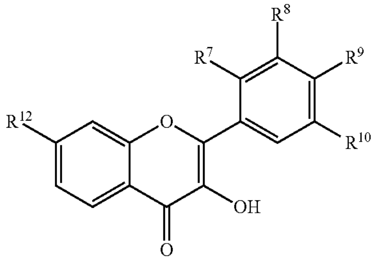

or a pharmaceutically acceptable salt thereof.

In certain embodiments of the compound of Formula IIe, or a pharmaceutically acceptable salt thereof, $R^7$ is H, $R^8$ is H, $R^9$ is H, $R^{10}$ is H, and $R^{12}$ is Br.

In certain embodiments of the compound of Formula IIe, or a pharmaceutically acceptable salt thereof, $R^7$ is H, $R^8$ is $OCH_3$, $R^9$ is H, $R^{10}$ is H, and $R^{12}$ is Br.

In certain embodiments of the compound of Formula IIe, or a pharmaceutically acceptable salt thereof, $R^7$ is H, $R^8$ is F, $R^9$ is OEt, $R^{10}$ is H, and $R^{12}$ is Cl.

In certain embodiments of the compound of Formula IIe, or a pharmaceutically acceptable salt thereof, $R^7$ is $OCH_3$, $R^8$ is H, $R^9$ is $OCH_3$, $R^{10}$ is $OCH_3$, and $R^{12}$ is Cl.

In certain embodiments, the fisetin agent has a structure of Formula IIf:

Formula IIf

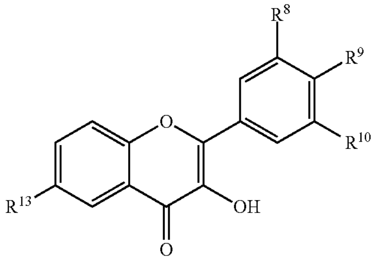

or a pharmaceutically acceptable salt thereof.

In certain embodiments of the compound of Formula IIf, or a pharmaceutically acceptable salt thereof, $R^8$ is H, $R^9$ is $OCH_3$, $R^{10}$ is $OCH_3$, and $R^{13}$ is Br.

In certain embodiments of the compound of Formula IIf, or a pharmaceutically acceptable salt thereof, $R^8$ is H, $R^9$ is Cl, $R^{10}$ is H, and $R^{13}$ is F.

In certain embodiments of the compound of Formula IIf, or a pharmaceutically acceptable salt thereof, $R^8$ is $OCH_3$, $R^9$ is $OCH_3$, $R^{10}$ is $OCH_3$, and $R^{13}$ is F.

In certain embodiments, the fisetin agent has a structure of Formula IIg:

Formula IIg

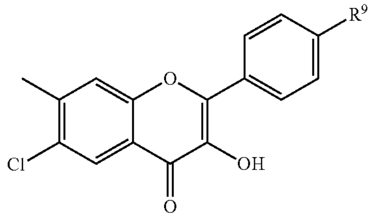

or a pharmaceutically acceptable salt thereof.

In certain embodiments of the compound of Formula IIg, or a pharmaceutically acceptable salt thereof, $R^9$ is t-Bu.

In certain embodiments of the compound of Formula IIg, or a pharmaceutically acceptable salt thereof, $R^9$ is OBn.

In certain embodiments, the fisetin agent has a structure of Formula IIh:

Formula IIh

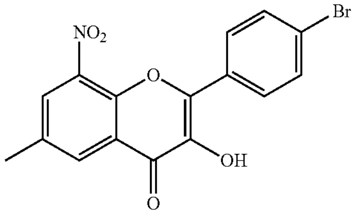

or a pharmaceutically acceptable salt thereof.

Nicotinamide Riboside

Nicotinamide riboside or a pharmaceutically acceptable salt thereof can be utilized for the treating or preventing (e.g., treating) of neurodegenerative diseases as disclosed herein.

Nicotinamide riboside is a member of the Vitamin B3 family and has the following structure:

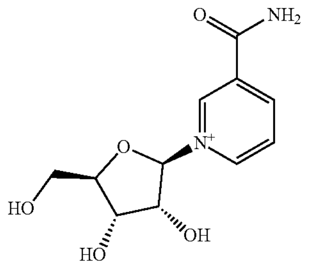 [SMILES: NC(=O)c1ccc[n+]([C@@H]2O[C@H](CO)[C@@H](O)[C@H]2O)c1]

Nicotinamide riboside is an $NAD^+$ precursor, which is an essential coenzyme that plays important roles in various metabolic pathways. The importance of $NAD^+$ is reflected through the activity of $NAD^+$-depleting enzymes, the mediators of aging, which are mostly induced by stress factors, such as DNA damage, oxidative stress, and inflammation. Pharmaceutically acceptable salts of nicotinamide riboside include, e.g., nicotinamide-β-d-riboside chloride, nicotinamide-β-d-riboside bromide, thionicotinamide-β-d-riboside bromide, nicotinamide-β-d-riboside triacetate bromide, and thionicotinamide-β-d-riboside triacetate bromide.

Nicotinamide riboside or pharmaceutically acceptable salts thereof are commercially available (e.g., Tru Niagen®) and can be obtained by methods known to the skilled artisan.

Cat's Claw

Cat's claw (*Uncaria tomentosa*) is a woody vine that can be found in the Amazon rain forest. Cat's claw extracts or components thereof can be utilized for the treating or preventing (e.g., treating) of neurodegenerative diseases as disclosed herein.

Cat's claw extracts can be prepared from cat's claw bark using conventional extraction methods. For example, the extraction process can involve use of 70% ethanol/distilled water at a ratio of 5:1. Components from cat's claw extracts can be isolated using conventional methods, including, e.g., affinity fractionation and high-pressure liquid chromatography (HPLC). The methods can also include assessment of the purity of the individual components using HPLC, mass spectroscopy and/or nuclear magnetic resonance (NMR) spectroscopy. The identity of individual components can be assessed using HPLC, −ve ion electrospray mass spectroscopy (relative intensity of the molecular ion given as a percentage), fourier transfer mass spectroscopy, ultraviolet spectroscopy, $^1H$ NMR, $^{13}C$ NMR, electrospray ionization time-of-flight mass spectroscopy (ESI-TOF), electron impact (EI) initiated mass spectroscopy, fast atom bombardment (FAB) mass spectroscopy, homonuclear correlation spectroscopy (COSY), constant time inverse-detection gradient accordion rescaled heteronuclear multiple bond correlation spectroscopy (CIGAR) and/or heteronuclear correlation spectroscopy (HETCOR).

In some embodiments, the cat's claw component is a polyphenol. In some embodiments, the cat's claw component is epicatechin dimers and variants thereof (known as proanthocyanidins). For example, the cat's claw component can be proanthocyanidin B2 (epicatechin-4ß-8-epicatechin), proanthocyanidin B4 (i.e. catechin-4α→8-epicatechin), proanthocyanidin C1 (i.e. epicatechin-4β→8-epicatechin-4β→8-epicatechin). In some embodiments, the cat's claw component is an epicatechin trimer (i.e. epicatechin-4β→8-epicatechin-4β→8-epicatechin), epiafzelechin-4β→8-epicatechin, or an epicatechin tetramer (i.e. epicatechin-4β→8-epicatechin-4β→8-epicatechin-4β→8-epicatechin). In some embodiments, the cat's claw extract is PTI-00703 (Percepta).

Methods of Treatment

Provided herein are methods of treating or preventing (e.g., treating) neurodegenerative diseases in a subject in need thereof by administering or otherwise delivering to the subject a urolithin A agent, and a fisetin agent, either individually or in combination. In some embodiments, the present disclosure provides a method of reducing pathogenic microglial pro-inflammatory activation in a subject, the method comprising administering to the subject a therapeutically effective amount of a urolithin A agent, and a therapeutically effective amount of a fisetin agent. In some embodiments, the present disclosure provides a method of promoting microglial Aβ clearance in a subject, the method comprising administering to the subject a therapeutically effective amount of a urolithin A agent, and a therapeutically effective amount of a fisetin agent. In some embodiments, the present disclosure provides a method of reducing pathogenic microglial pro-inflammatory activation and promoting microglial Aβ clearance in a subject, the method comprising administering to the subject a therapeutically effective amount of a urolithin A agent, and a therapeutically effective amount of a fisetin agent.

Thus, among other things, the present disclosure documents that provided technologies (e.g., combinations of a urolithin A agent and a fisetin agent achieve reduction in inflammation, including specifically of microglial inflammation. In some embodiments, the present disclosure documents that such provided technologies reduce pro-inflammatory activation, e.g., microglial pro-inflammatory activation, specifically including pathogenic microglial pro-inflammatory activation.

In many embodiments, provided methods involve combination therapy with at least a urolithin A agent and a fisetin agent. Those skilled in the art will appreciate that combination therapy (e.g., urolithin A agent and fisetin agent combination therapy) involves administration or other delivery of one or more of a plurality of agents to a subject, so that the subject is exposed to all of them. In some embodiments, each agent of the combination is administered or otherwise delivered to the subject. In some embodiments, one or more agents is administered or otherwise delivered to a subject who has already received, is receiving, or will receive (e.g., via an overlapping administration regimen) the remaining agent(s) of the combination.

In some embodiments, combination therapy involves administration of one or more pharmaceutical compositions as described herein (i.e., that comprise and/or otherwise deliver a relevant agent as described herein), each of which comprises and/or delivers one or more agent(s) of a combination. In some embodiments, different agent(s) are delivered from different pharmaceutical compositions (i.e., from distinct dosage forms). In some embodiments, two or more agents may be delivered from the same pharmaceutical composition (i.e., may be included in the same dosage form). In some embodiments, pharmaceutical compositions that delivery different agents are administered according to overlapping dosing regimens, determined to achieve exposure to all agents of a combination.

In some embodiments, provided methods include administration or other delivery of one or more agents in addition to urolithin A agents and fisetin agents; in particular embodiment, such one or more additional agents is one or both of nicotinamide riboside or pharmaceutically acceptable salts thereof, and cat's claw extracts or components thereof. In some embodiments, provided methods include administering a combination of urolithin A agents and fisetin agents. In some embodiments, provided methods include administering a combination of urolithin A agents, fisetin agents, and a cat's claw extract or component thereof. In some embodiments, provided methods include administering a combination of urolithin A agents, fisetin agents, and nicotinamide riboside or a pharmaceutically acceptable salt thereof. In some embodiments, provided methods include administering a combination of urolithin A agents, fisetin agents, nicotinamide riboside or a pharmaceutically acceptable salt thereof and a cat's claw extract or component thereof. For example, in some embodiments, provided methods include administering a combination of urolithin A, fisetin, and quercetin. In some embodiments, provided methods include administering a combination of urolithin A, fisetin and a cat's claw extract or component thereof. In some embodiments, provided methods include administering a combination of urolithin A, fisetin, quercetin, and a cat's claw extract or component thereof. In some embodiments, provided methods include administering a combination of urolithin A, fisetin, quercetin, and nicotinamide riboside or a pharmaceutically acceptable salt thereof. In some embodiments, provided methods include administering a combination of urolithin A, fisetin, nicotinamide riboside or a pharmaceutically acceptable salt thereof, and a cat's claw extract or component thereof. In some embodiments, provided methods include administering a combination of urolithin A, fisetin, quercetin, nicotinamide riboside or a pharmaceutically acceptable salt thereof, and a cat's claw extract or component thereof.

Also provided herein are methods of treating or preventing (e.g., treating) neurodegenerative diseases in a subject in need thereof, comprising administering or otherwise delivering to the subject an ellagitannin or ellagic acid, or an analog or metabolite thereof, alone or in combination with a fisetin agent, wherein the method can further include determining or having determined that the subject is a urolithin A producer. In some embodiments, provided methods include administration or other delivery of one or more agents in addition to an ellagitannin or ellagic acid, or an analog or metabolite thereof and fisetin agents; in particular embodiment, such one or more additional agents is one or both of nicotinamide riboside or pharmaceutically acceptable salts thereof, and cat's claw extracts or components thereof.

In some embodiments, provided methods include administering a combination of an ellagitannin or ellagic acid, or an analog or metabolite thereof and fisetin agents. In some embodiments, provided methods include administering a combination of an ellagitannin or ellagic acid, or an analog or metabolite thereof, fisetin agents, and a cat's claw extract or component thereof. In some embodiments, provided methods include administering a combination of an ellagitannin or ellagic acid, or an analog or metabolite thereof, fisetin agents, and nicotinamide riboside or a pharmaceutically acceptable salt thereof. In some embodiments, provided methods include administering a combination of an ellagitannin or ellagic acid, or an analog or metabolite thereof, fisetin agents, nicotinamide riboside or a pharmaceutically acceptable salt thereof and a cat's claw extract or component thereof. For example, in some embodiments, provided methods include administering a combination of an ellagitannin or ellagic acid, or an analog or metabolite thereof, fisetin, and quercetin. In some embodiments, provided methods include administering a combination of an ellagitannin or ellagic acid, or an analog or metabolite thereof, fisetin and a cat's claw extract or component thereof. In some embodiments, provided methods include administering a combination of an ellagitannin or ellagic acid, or an analog or metabolite thereof, fisetin, quercetin, and a cat's claw extract or component thereof. In some embodiments, provided methods include administering a combination of an ellagitannin or ellagic acid, or an analog or metabolite thereof, fisetin, quercetin, and nicotinamide riboside or a pharmaceutically acceptable salt thereof. In some embodiments, provided methods include administering a combination of an ellagitannin or ellagic acid, or an analog or metabolite thereof, fisetin, nicotinamide riboside or a pharmaceutically acceptable salt thereof, and a cat's claw extract or component thereof. In some embodiments, provided methods include administering a combination of an ellagitannin or ellagic acid, or an analog or metabolite thereof, fisetin, quercetin, nicotinamide riboside or a pharmaceutically acceptable salt thereof, and a cat's claw extract or component thereof.

The present disclosure also provides methods of treating neurodegenerative diseases in a subject in need thereof, comprising administering or otherwise delivering to the subject an ellagitannin or ellagic acid, or an analog or metabolite thereof, alone or in combination with a fisetin agent, where the method can further include administering a composition comprising one or more bacterial species that are associated with urolithin A production. In some embodiments, provided methods include administration or other delivery of one or more agents in addition to an ellagitannin or ellagic acid, or an analog or metabolite thereof and fisetin agents; in particular embodiment, such one or more additional agents is one or both of nicotinamide riboside or pharmaceutically acceptable salts thereof, and cat's claw extracts or components thereof.

In some embodiments, provided methods include administering a combination of an ellagitannin or ellagic acid, or an analog or metabolite thereof and fisetin agents. In some embodiments, provided methods include administering a combination of an ellagitannin or ellagic acid, or an analog or metabolite thereof, fisetin agents, and a cat's claw extract or component thereof. In some embodiments, provided methods include administering a combination of an ellagitannin or ellagic acid, or an analog or metabolite thereof, fisetin agents, and nicotinamide riboside or a pharmaceutically acceptable salt thereof. In some embodiments, provided methods include administering a combination of an ellagitannin or ellagic acid, or an analog or metabolite thereof, fisetin agents, nicotinamide riboside or a pharmaceutically acceptable salt thereof and a cat's claw extract or component thereof. For example, in some embodiments, provided methods include administering a combination of an ellagitannin or ellagic acid, or an analog or metabolite thereof, fisetin, and quercetin. In some embodiments, provided methods include administering a combination of an ellagitannin or ellagic acid, or an analog or metabolite thereof, fisetin and a cat's claw extract or component thereof. In some embodiments, provided methods include administering a combination of an ellagitannin or ellagic acid, or an analog or metabolite thereof, fisetin, quercetin, and a cat's claw extract or component thereof. In some embodiments, provided methods include administering a combination of an ellagitannin or ellagic acid, or an analog or metabolite thereof, fisetin, quercetin, and nicotinamide riboside or a pharmaceutically acceptable salt thereof. In some embodiments, provided methods include administering a combination of an ellagitannin or ellagic acid, or an analog or metabolite thereof, fisetin, nicotinamide riboside or a pharmaceutically acceptable salt thereof, and a cat's claw extract or component thereof. In some embodiments, provided methods include administering a combination of an ellagitannin or ellagic acid, or an analog or metabolite thereof, fisetin, quercetin, nicotinamide riboside or a pharmaceutically acceptable salt thereof, and a cat's claw extract or component thereof.

Also provided herein are methods of treating or preventing (e.g., treating) neurodegenerative diseases in a subject in need thereof by administering or otherwise delivering to the subject two or more agents selected from a urolithin A agent, a fisetin agent, nicotinamide riboside or a pharmaceutically acceptable salt thereof, or a cat's claw extract or component thereof. For example, the method can include administering a urolithin A agent in combination with a cat's claw extract or component thereof, with or without nicotinamide riboside or a pharmaceutically acceptable salt thereof.

Non-limiting examples of neurodegenerative diseases that can be treated or prevented using the methods disclosed herein include Alzheimer's disease (AD), Parkinson's disease, Huntington's Disease, Amyotrophic Lateral Sclerosis, Multiple Sclerosis, polyglutamine expansion disorders (e.g., HD, dentatorubropallidoluysian atrophy, Kennedy's disease (also referred to as spinobulbar muscular atrophy), spinocerebellar ataxia (e.g., type 1, type 2, type 3 (also referred to as Machado-Joseph disease), type 6, type 7, and type 17)), other trinucleotide repeat expansion disorders (e.g., fragile X syndrome, fragile XE mental retardation, Friedreich's ataxia, myotonic dystrophy, spinocerebellar ataxia type 8, and spinocerebellar ataxia type 12), Alexander disease, Alper's disease, ataxia telangiectasia, Batten disease (also referred to as Spielmeyer-Vogt-Sjogren-Batten disease), Canavan disease, Cockayne syndrome, corticobasal degeneration, Creutzfeldt-Jakob disease, ischemia stroke, Krabbe disease, Lewy body dementia, multiple system atrophy, Pelizaeus-Merzbacher disease, Pick's disease, primary lateral sclerosis, Refsum's disease, Sandhoff disease, Schilder's disease, spinal cord injury, spinal muscular atrophy, SteeleRichardson-Olszewski disease, and Tabes dorsalis.

As is understood by those skilled in the art, effective prevention can involve delay of onset (e.g., of expected onset, as may be determined, for example, based on genetic, lifestyle, biomarker, or other factor(s)) of one or more features of a relevant disease, disorder or condition (e.g., of a neurodegenerative disease, as described herein); effective treatment can involve delay of onset (e.g., of expected onset) and/or reduction in frequency and/or severity of one or more such features.

Methods described in the present disclosure can include treatment of a disease or disorder per se, as well as treatment for one or more symptoms of the disease or disorder. "Treating" a disease does not require 100% abolition of the disease or disease symptoms in the subject. In some embodiments, treatment achieves relief or reduction in severity of one or more symptoms or features of the disease; typically, relevant relief or reduction is determined, for example, by a significant effect in an appropriate system (e.g., a model system) and/or an appropriate population (e.g., of human subjects or of animal models). In some embodiments, "treating" may be or comprise a delay in onset of symptoms or delay in progression of symptoms or the loss of function associated with the disease; alternatively or additionally, in some embodiments, "treating" may be or comprise a reduction in frequency and/or severity of one or more symptoms or features of the disease; alternatively or additionally, "treating" may be or comprise eliminating or reducing one or more side effects of a treatment or eliminating or reducing one or more direct or indirect effects of disease progression. In some embodiments, a subject who receives treatment in accordance with the present disclosure may not exhibit signs of the disease but may be at risk for the disease.

In some embodiments, provided methods include selection of a subject, for example, by obtaining a sample from a candidate subject and testing the sample for an indication that the subject is suitable for selection. In some instances, the subject can be confirmed or identified, e.g. by a health care professional, as having a condition or disease or at risk for developing the condition or disease. In some instances multiple parties can be included in subject selection. For example, a first party can obtain a sample from a candidate subject and a second party can test the sample. In some instances, subjects can be selected and/or referred by a medical practitioner (e.g., a general practitioner). Samples can include, for example, cells or populations of cells.

The terms "administer", "administering", or "administration" as used herein refers to causing a subject to receive (i.e., to be exposed to) a relevant agent and, in some embodiments, can involve one or more of, e.g., ingesting, injecting, implanting, absorbing, or inhaling, the agent, without restriction to a particular form. In some embodiments, one or more of the compounds disclosed herein can be administered to a subject by ingestion orally and/or topically (e.g., nasally). For example, in some embodiments, provided methods include administration of an effective amount of an agent or combination of agents to achieve the desired or stated effect. Specific dosage and treatment regimens for any particular subject may depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Those skilled in the art, reading the present specification, will appreciate that, where combination therapy is involved, an "effective amount" of a particular agent included in the combination therapy is an amount that is effective (e.g., has been demonstrated to be effective, for example, through appropriate testing in relevant system(s) [e.g., model system(s)] and/or population(s) [e.g., patient population(s)]; where an amount has been demonstrated to be effective in a particular model system, those skilled in the art will be aware that appropriate adjustment establishes a corresponding amount for delivery [e.g., administration] to a subject [e.g., a human subject]) in the context of such combination; such amount may be different from, and in particular embodiments may be lower than and/or less frequent than, that which would be required to achieve a particular effect if such agent were delivered other than as part of relevant combination therapy.

In some embodiments, following administration, the subject can be evaluated to detect, assess, or determine their level of disease. In some embodiments, treatment can continue until a change (e.g., reduction) in the level of disease in the subject is detected. In some embodiments, treatment methods can include assessing a level of disease in the subject prior to treatment, during treatment, and/or after treatment.

Upon improvement of a patient's condition (e.g., a change (e.g., decrease) in the level of disease in the subject), a maintenance dose of a compound, composition or combination of this disclosure may be administered, if necessary or desired. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

The term "subject," as used herein, refers to any animal. In some instances, the subject is a mammal. In some instances, the term "subject", as used herein, refers to a human (e.g., a man, a woman, or a child).

Alzheimer's Disease

In some embodiments, the neurodegenerative disease is Alzheimer's disease (AD). Alzheimer's disease is characterized by the loss of neurons and synapses in the cerebral cortex and atrophy in the temporal and parietal lobes. Histopathological findings of AD can include abnormal aggregates of amyloid plaques and neurofibrillary tangles.

Provided herein are methods of treating Alzheimer's disease in a subject in need thereof, comprising administering to the subject a combination of a urolithin A agent and a fisetin agent. The methods can be used to treat at least one symptom of AD, reduce AD disease progression, reduce the deterioration of, maintain, or improve one or more bodily functions affected by AD, treat dementia or mild cognitive impairment (MCI) (e.g. dementia or MIC due to AD), or reduce the progressive decline of cognitive functions, including loss of declarative and procedural memory, decreased learning ability, reduced attention span, severe impairment in thinking ability, judgment, and decision making. Also provided are methods of increasing the survival time of a subject having one or more symptoms of AD or reducing the levels of one or more biomarkers in a subject with AD (e.g., total tau or phospho-tau).

In certain embodiments, the subject exhibits one or more symptoms associated with AD, have been diagnosed with AD, be suspected as having AD, or at risk for developing AD. The methods of treatment can further include determining or having determined that a subject has AD, has one or more symptoms associated with AD, or is at risk for developing AD.

Methods of diagnosing AD are known in the art. The subject can be diagnosed based on clinical history, family history, physical or neurological examinations. The subject can be confirmed or identified by a healthcare professional as having AD. Diagnosis of AD or determination of the risk of developing AD can be based upon neuroimaging, one or more cognitive tests (e.g., ADAS-Cog, MoCA, DSRS, MADCOMS, FAQ, or NPI-Q), or the presence of one or more biomarkers in the subject's cerebrospinal fluid or blood samples. Exemplary biomarkers include amyloid-β 42 (Aβ42), total tau (T-tau), phosphorylated tau (P-tau), Aβ42/40 or amyloid precursor protein (APP) 669-711/Aβ42 ratios, neurogranin, neurofilament light, and soluble insulin receptor. Diagnosis can also be based on detection of mutations in one or more genes associated with AD, for example, the presence of APOEε4 alleles or mutations in APP, Presenilin 1 (PSEN1), or Presenilin 2 (PSEN2). Inflammation within the brain, including increased reactivity of the resident microglia towards amyloid deposits, has been implicated in the pathogenesis and progression of AD. Therefore, diagnosis can also be based on the presence of markers of neuro-inflammation.

The treatment provided in the present disclosure can be initiated at any stage during disease progression. For example, treatment can be initiated prior to onset (e.g., for subjects at risk for developing AD), at symptom onset or immediately following detection of AD symptoms, or upon observation of any one or more symptoms that would lead a skilled practitioner to suspect that the subject may be developing AD (e.g., decline in cognitive functions, memory loss, reduced attention span). Treatment can also be initiated at later stages.

Administration of Ellagitannin or Ellagic Acid

The present disclosure also provides methods of treating or preventing (e.g., treating) neurodegenerative diseases in a subject in need thereof, comprising administering or otherwise delivering to the subject an ellagitannin (e.g., any ellagitannin disclosed herein or known in the art) or ellagic acid, or an analog or metabolite thereof, and a fisetin agent, wherein the method can further include determining or having determined that the subject is a urolithin A producer.

Whether a subject is a urolithin A producer can be determined based on the presence of one or more bacterial species in their gut microbiota (e.g., from blood, urine or fecal samples) that are associated with urolithin A production. Bacterial species that are associated with urolithin A production can be those known in the art, including, for example, those belonging to the Clostridiales and Ruminococcaceae family, and *Gordonibacter urolithinfaciens, Ellagibacter isourolithinifaciens*, and *Akkermansia muciniphilia.*

Also provided herein are methods of treating or preventing (e.g., treating) neurodegenerative diseases in a subject in need thereof, comprising administering to the subject an ellagitannin or ellagic acid, or an analog or metabolite thereof, in combination with a fisetin agent, and a composition comprising one or more bacterial species that are associated with urolithin A production (e.g., any of the bacteria species disclosed herein or known in the art). A bacterial composition can be prepared in a variety of forms, such as capsules, tablets, suppositories, food, or drink. The ellagitannin or ellagic acid, or the analog or metabolite thereof, the fisetin agent, and the composition comprising one or more bacterial species can be administered concurrently or separately and can be administered at the same or different frequencies.

Dosing

The compounds of the present disclosure can generally be administered in a therapeutically effective amount. An "effective amount" is an amount sufficient to effect beneficial or desired results. For example, a therapeutically effective amount can be one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

In some embodiments, a provided therapy is a regulated therapy, wherein its commercialization is supported by clinical trial(s) and/or is otherwise subjected to government regulation and/or oversight. Alternatively or additionally, in some embodiments, a provided therapy may be commercialized without regulatory review and/or approval.

The data obtained from cell culture assays and animal studies can be used in formulating a range of dosage for use in humans. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The agents provided herein can be administered separately or concurrently, including as a part of a regimen of treatment. For example, urolithin A agents, fisetin agents, and one or more additional agents (e.g., nicotinamide riboside or pharmaceutically acceptable salts thereof or cat's claw extracts or components thereof) disclosed herein can be administered separately in separate dosage forms, or concurrently as part of a single dosage form. The agents provided herein can be administered daily, weekly, monthly, or quarterly. In some embodiments, they are administered once a day, twice a day, or three times a day or more. They can be administered over a period of weeks, months, or years. For example, the compounds can be administered over a period of at least or about 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, or at least or about 5 years, or more.

Urolithin A has been reported to be safe and/or useful when administered in those amounts within a range of 500 mg to 1000 mg daily (see e.g., Cell Rep Med. 2022 May 17; 3(5): 100633). In some embodiments, urolithin A may be administered or delivered in such amounts and/or according to such regimens in accordance with the present disclosure. Alternatively or additionally, in some embodiments, urolithin A may be utilized in accordance with the present disclosure in alternative dose amount and/or according to alternative regimens. For example, in some embodiments, urolithin A may be utilized in lower dose amount(s) and/or with less frequent administration than that at which it has been utilized when administered alone.

Urolithin A can be administered at a dose of about 1 mg to about 2500 mg (e.g., about 1 mg to about 1000 mg, about 50 mg to about 2500 mg, about 10 mg to about 2400 mg, about 100 mg to about 2300 mg, about 130 mg to about 2100 mg, about 160 mg to about 1900, about 190 mg to about 1700 mg, about 220 mg to about 1500 mg, about 240 mg to about 1300 mg, about 260 mg to about 1100 mg, about 280 mg to about 1000 mg, about 300 mg to about 900 mg, about 1 mg, about 10 mg, about 50 mg, about 75 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg). Urolithin A can be administered once a day, twice a day, or three or more times a day. For example, urolithin A can be administered at a dose of about 50 mg to about 2500 mg (e.g. any of the subranges or doses within this range disclosed herein) twice a day. Urolithin A can be administered at an amount of about 100 mg to about 5000 mg daily (e.g., about 200 mg to about 4000 mg, about 300 mg to about 3000 mg, about 400 mg to about 2500 mg, about 500 mg to about 2000 mg, about 550 mg to about 1500 mg, about 600 mg to about 1200 mg, about 700 mg to about 1100 mg, about 750 mg, about 800 mg, about 850 mg, about 900 mg, about 950 mg, or about 1000 mg daily). In some embodiments, urolithin A is administered at an amount of about 1000 mg daily (e.g., about 500 mg twice a day). In some embodiments, urolithin A is administered in an amount that is from about 1 mg to about 1000 mg per day.

In some embodiments, urolithin A is administered at a dose of about 0.5 to about 65 mg/kg of the subject's body weight (e.g., about 1 to about 60, about 1.5 to about 55, about 2 to about 50, about 2.5 to about 45, about 3 to about 40, about 3.5 to about 35, about 4 to about 30, about 4.5 to about 25, about 5 to about 20, about 5.5 to about 15, about 6 to about 12, or about 6.5 to about 10 mg/kg of the subject's body weight).

Urolithin A agents other than urolithin A can be administered at a dose that corresponds with a dose for urolithin A as disclosed herein, where correspondence can be established, for example, by comparable results and in appropriate assessment, as will be understood by those skilled in the art.

Fisetin can be administered at a dose of about 0.5 mg to about 2500 mg (e.g., about 0.5 mg to about 20 mg, about 1 mg to about 10 mg, about 2 mg to about 6 mg, about 25 mg to about 500 mg, about 50 mg to about 300 mg, about 100 mg to about 200 mg, about 200 mg to about 1500 mg, about 300 mg to about 1200 mg, or about 400 mg to about 750 mg). Fisetin can be administered once a day, twice a day, or three or more times a day. For example, fisetin can be administered at a dose of about 0.5 mg to about 2000 mg (e.g. any of the subranges or doses within this range disclosed herein) twice a day. Fisetin can be administered at an amount of about 1 mg to about 5000 mg daily (e.g., about 1 mg to about 40 mg, about 2 mg to about 20 mg, about 4 mg to about 12 mg, about 50 mg to about 1000 mg, about 100 mg to about 800 mg, about 150 mg to about 500 mg, about 200 mg to about 400 mg, about 500 mg to about 2000 mg, about 700 mg to about 1800 mg, or about 800 mg to about 1500 mg daily). In some embodiments, fisetin is administered at an amount of about 8 mg daily (e.g., about 4 mg twice a day).

Fisetin agents other than fisetin can be administered at a dose that corresponds with a dose for fisetin as disclosed herein, where correspondence can be established, for example, by comparable results and in appropriate assessment, as will be understood by those skilled in the art.

In some embodiments, fisetin is administered at an amount of about 0.05 to about 60 mg/kg of the subject's body weight (e.g., about 0.05 to about 0.15, about 0.4 to about 12, about 0.6 to about 10, about 0.8 to about 8, about 1 to about 6, about 1.5 to about 26, about 2 to about 24, about 2.5 to about 22, or about 3 to about 20 mg/kg of the subject's body weight).

In some embodiments, when administered in combination with urolithin A for treating or preventing (e.g., treating) a neurodegenerative disease, the dosage of fisetin can be reduced as compared to the dosage used when fisetin is administered alone. For example, the amount of fisetin administered in combination with urolithin A can be reduced by about 5%, about 10%, about 15%, about 20%, about 25%, about 30%, about 40%, about 50%, or about 55% compared to the dosage used when fisetin is administered alone.

In some embodiments, when administered in combination with fisetin for treating or preventing (e.g., treating) a neurodegenerative disease, the dosage of urolithin A can be reduced as compared to the dosage used when urolithin A is administered alone. For example, the amount of urolithin A administered in combination with fisetin can be reduced by about 5%, about 10%, about 15%, about 20%, about 25%, about 30%, about 40%, about 50%, or about 55% compared to the dosage used when urolithin A is administered alone.

In some embodiments, urolithin A is administered at an amount of about 1 mg to about 1100 mg daily and fisetin is administered at an amount of about 4 mg to about 12 mg daily. In some embodiments, urolithin A is administered in an amount that is about 100 mg to about 1000 mg per day and fisetin is administered in an amount that is about 4 mg to about 12 mg per day.

Nicotinamide riboside can be administered at a dose of about 1 mg to about 2500 mg (e.g., about 10 mg to about 1000 mg about 50 mg to about 900 mg, about 100 mg to about 800 mg, about 200 mg to about 700 mg, about 300 mg to about 600 mg, or about 500 mg). For example, nicotinamide riboside can be administered at a dose of about 200 mg, 300 mg, 400 mg, 500 mg, 600 mg, or 700 mg per day.

Cat's claw extracts can be administered at a dose of about 1 mg to about 2500 mg (e.g., about 100 mg to about 1200 mg about 200 mg to about 1100 mg, about 300 mg to about 1000 mg, about 400 mg to about 900 mg, about 600 mg to about 800 mg, or about 750 mg).

Quercetin can be administered at a dose of about 1 mg to about 2500 mg (e.g., about 50 mg to about 1000 mg about 50 mg to about 800 mg, about 100 mg to about 600 mg, about 150 to about 500 mg, about 200 mg to about 300 mg, or about 250 mg). For example, quercetin can be administered at a dose of about 200 mg, about 250 mg, about 300 mg, or about 400 mg once a day or twice a day.

In some embodiments, when administering urolithin A and fisetin in combination with one or more of nicotinamide riboside, cat's claw, or quercetin for treating a neurodegenerative disease, the dosage of urolithin A or fisetin can be reduced as compared to the dosage used when only administering urolithin A and fisetin. For example, the amount of urolithin A or fisetin can be reduced by about 5%, about 10%, about 15%, about 20%, about 25%, about 30%, about 40%, about 50%, or about 55%.

Pharmaceutical Composition

When employed as pharmaceuticals, agents of the disclosure can be administered in the form of pharmaceutical compositions which comprise and/or deliver relevant compound(s).

A pharmaceutical composition refers to a combination of one or more compounds of the present disclosure, and at least one pharmaceutically acceptable carrier.

For example, the present disclosure provides pharmaceutical compositions comprising one or more agents selected from urolithin A agent, fisetin agents, nicotinamide riboside or pharmaceutically acceptable salts thereof, and cat's claw extracts or components thereof, individually or in combination, and optionally comprising one or more excipients. In some embodiments, the provided pharmaceutical compositions comprise a combination of urolithin A agents and fisetin agents, and optionally comprising one or more excipients. In some embodiments, the provided pharmaceutical compositions comprise urolithin A, fisetin and optionally one or more excipients. In some embodiments, the provided pharmaceutical compositions comprise urolithin A, quercetin, and optionally one or more excipients. In some embodiments, the provided pharmaceutical compositions comprise urolithin A, fisetin and one or more of an agent selected from quercetin, nicotinamide riboside or a pharmaceutically acceptable salt thereof, and cat's claw extracts or components thereof, and optionally one or more excipients. These compositions can be prepared in a manner well known in the pharmaceutical art, and can be administered by a variety of routes, depending upon whether local or systemic treatment is desired and upon the area to be treated.

Pharmaceutical compositions are typically formulated to be compatible with its intended route of administration. Examples of routes of administration include parenteral (subcutaneous, intracutaneous, intravenous, intradermal, intramuscular, intra-articular, intraarterial, intrasynovial, intrasternal, intrathecal, intralesional and intracranial injection or infusion techniques), oral (e.g., inhalation), transdermal (topical), transmucosal, and rectal administration.

Pharmaceutical compositions can be in the form of a solution or powder. Suitable powders may include those that are substantially soluble in water. Pharmaceutical compositions may be formulated according to techniques known in the art using suitable dispersing or wetting agents (such as, for example, Tween 80) and suspending agents.

Pharmaceutical compositions can be orally administered in any orally acceptable dosage form including, but not limited to, powders, capsules, tablets, emulsions and aqueous suspensions, dispersions and solutions, or hydrogel formulations. In the case of powders for oral administration, the powders can be substantially dissolved in water prior to administration. In the case of tablets for oral use, carriers which are commonly used include lactose and corn starch. Lubricating agents, such as magnesium stearate, may be added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening, flavoring, or coloring agents may be added.

Pharmaceutical compositions can also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some embodiments, provided herein are oral compositions comprising one or more agents selected from urolithin A agents, fisetin agents, nicotinamide riboside or pharmaceutically acceptable salts thereof, and cat's claw extracts or components thereof, optionally comprising one or more excipients. In some embodiments, the oral composition is capsules, soft gels, or tablets.

The pharmaceutical compositions can be included in a container, pack, or dispenser together with instructions for administration. In some embodiments, the invention provides kits that include the bile acid and phenylbutyrate compounds. The kit may also include instructions for the physician and/or patient, syringes, needles, box, bottles, vials, etc.

Combination Therapy

As discussed herein and understood by those skilled in the art, combination therapy (e.g., urolithin A agent and fisetin agent combination therapy) involves administration or other delivery of one or more of a plurality of agents to a subject, so that the subject is exposed to all of them. In some embodiments, each agent of the combination is administered or otherwise delivered to the subject. In some embodiments, one or more agents is administered or otherwise delivered to a subject who has already received, is receiving, or will receive (e.g., via an overlapping administration regimen) the remaining agent(s) of the combination.

In some embodiments, combination therapy involves administration of one or more pharmaceutical compositions (i.e., that comprise and/or otherwise deliver an active agent, e.g., as described herein), each of which comprises and/or delivers one or more agent(s) of a combination. In some embodiments, different agent(s) are delivered from different pharmaceutical compositions (i.e., from distinct dosage forms). In some embodiments, two or more agents may be delivered from the same pharmaceutical composition (i.e., may be included in the same dosage form). In some embodiments, pharmaceutical compositions that delivery different agents are administered according to overlapping dosing regimens, determined to achieve exposure to all agents of a combination.

In some embodiments, combination therapy in accordance with the present disclosure is or comprises urolithin A agent and fisetin agent combination therapy. In some embodiments, combination therapy involves combination of a urolithin A agent and/or a fisetin agent with one or more additional therapeutic agents. As noted, in some embodiments, such additional therapeutic agents can be combined with the compounds disclosed herein in a single dosage form, or the agents can be administered simultaneously or sequentially as separate dosage forms. In some embodiments, additional agents include those known for treating or preventing (e.g., treating) neurodegenerative diseases. For example, in some embodiments, suitable agents for use in combination therapy as described herein may include one or more of donepezil (Aricept®), tacrine (Cognex®), rivastigmine (Exelon®), galantamine (Nivalin® and Razadyne®), memantine (Namenda®), anti-amyloid vaccine, Aβ-lowering therapies, and mental exercise or stimulation.

In some cases, treatment with a urolithin A agent and/or a fisetin agent as described herein may reduce the need for treatment with one or more additional therapeutic agents or reduce the dose or frequency required for the additional therapeutic agents to obtain the same treatment effect. For example, the amount of the additional therapeutic agent administered to the subject can be reduced by at least about 10% (e.g., at least about 15%, 20%, 25%, 30%, 35%, 40%, 45%, 50%, or 55%) compared to the dosage amount used when the additional therapeutic agent(s) is administered alone.

EXAMPLES

The following examples are provided by way of illustration of certain embodiments of the present disclosure and are not in any way intended to limit the scope of this disclosure or the claims.

Example 1: Effects of Urolithin a and Fisetin on Microglial Aß Clearance and the Release of Pro-Inflammatory Cytokines Urolithin A was identified as a top-tier enhancer of Aß clearance by microglia in an unbiased (and biased) screening of natural product compounds. Cellular assay models based on BV2 microglial cells were used to assess the ability of microglia to phagocytose synthetic Aß42 peptides, a major pathogenic Aß isoform of Alzheimer's disease Aß species (microglial uptake/clearance). FIG. 1 shows a representative result where urolithin A increases microglial Aß uptake/clearance in a dose-dependent manner in the cell culture model. $EC_{50}$ for Aß42 uptake is 1.243e-005 M in this model system. As shown in FIG. 3, microglial Aß uptake/clearance is dramatically increased by co-treatment of urolithin A and fisetin, as compared to fisetin alone.

Figure 2A:
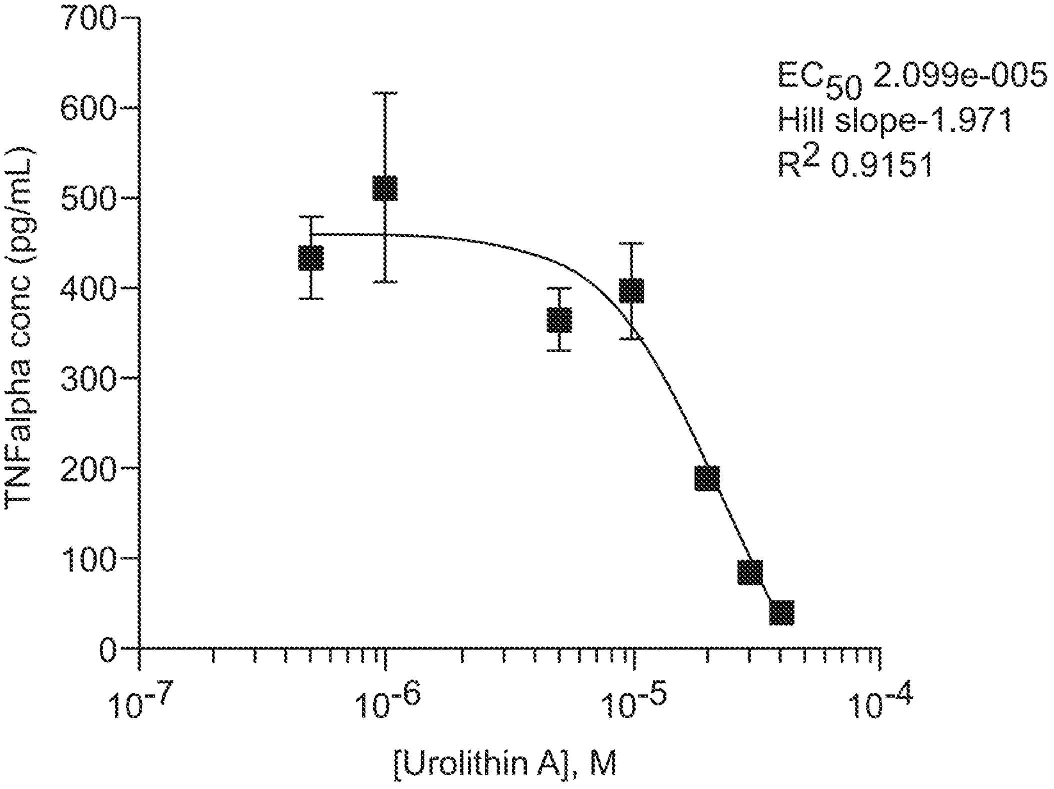

Effects of urolithin A and fisetin on the reduction of pro-inflammatory cytokines levels, such as TNFα, were assessed in an unbiased library screening. BV2 microglial cells were converted to a pro-inflammatory activation state by acute treatment with 1 μg/mL of Lipopolysaccharide (LPS) for 5 hours in the presence of a vehicle or urolithin A or fisetin. Effects on inflammation were assessed by measuring levels of a representative pro-inflammatory cytokine, TNFα, via an ELISA assay on the conditioned cell media. FIGS. 2A and 2B show representative results of the dose-response reduction of TNFα after treatment with LPS and urolithin A and fisetin, respectively. While each of urolithin A and fisetin reduce TNFα release by LPS-activated microglia in a dose-dependent manner, fisetin has an $EC_{50}$ of 8 μM and urolithin A of 21 M, indicating that fisetin is a more effective drug in this assay.

Figure 4A:
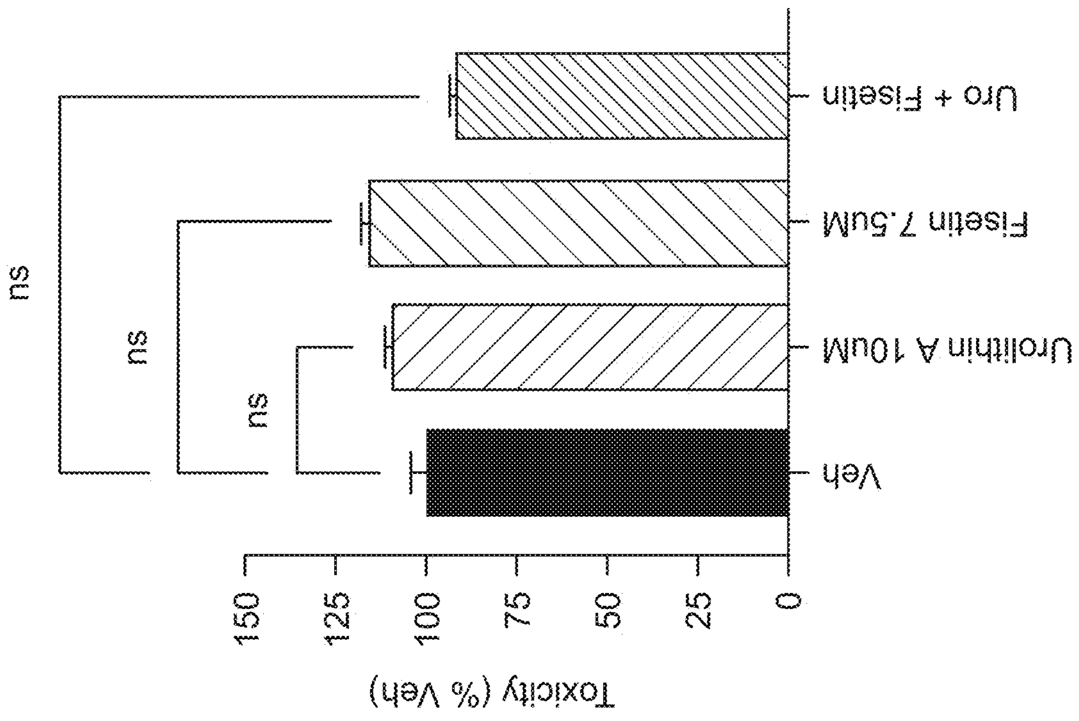
FIGS. 4A and 4B show toxicity and TNFα levels in BV2 microglial cells in response to treatment with urolithin A and fisetin, alone or in combination.

Next, BV2 microglial cells were treated with urolithin A at 10 μM and fisetin at 7.5 μM, alone or in combination. Drug toxicity during cell treatment was measured by monitoring the levels of lactate dehydrogenase released in the conditioned media, expressed as Vehicle % (FIG. 4A). The combination treatment did not impact cell viability as shown in FIG. 4A. Reduction of TNFα in BV2 microglial cells was measured by ELISA (FIG. 4B).

Figure 5:
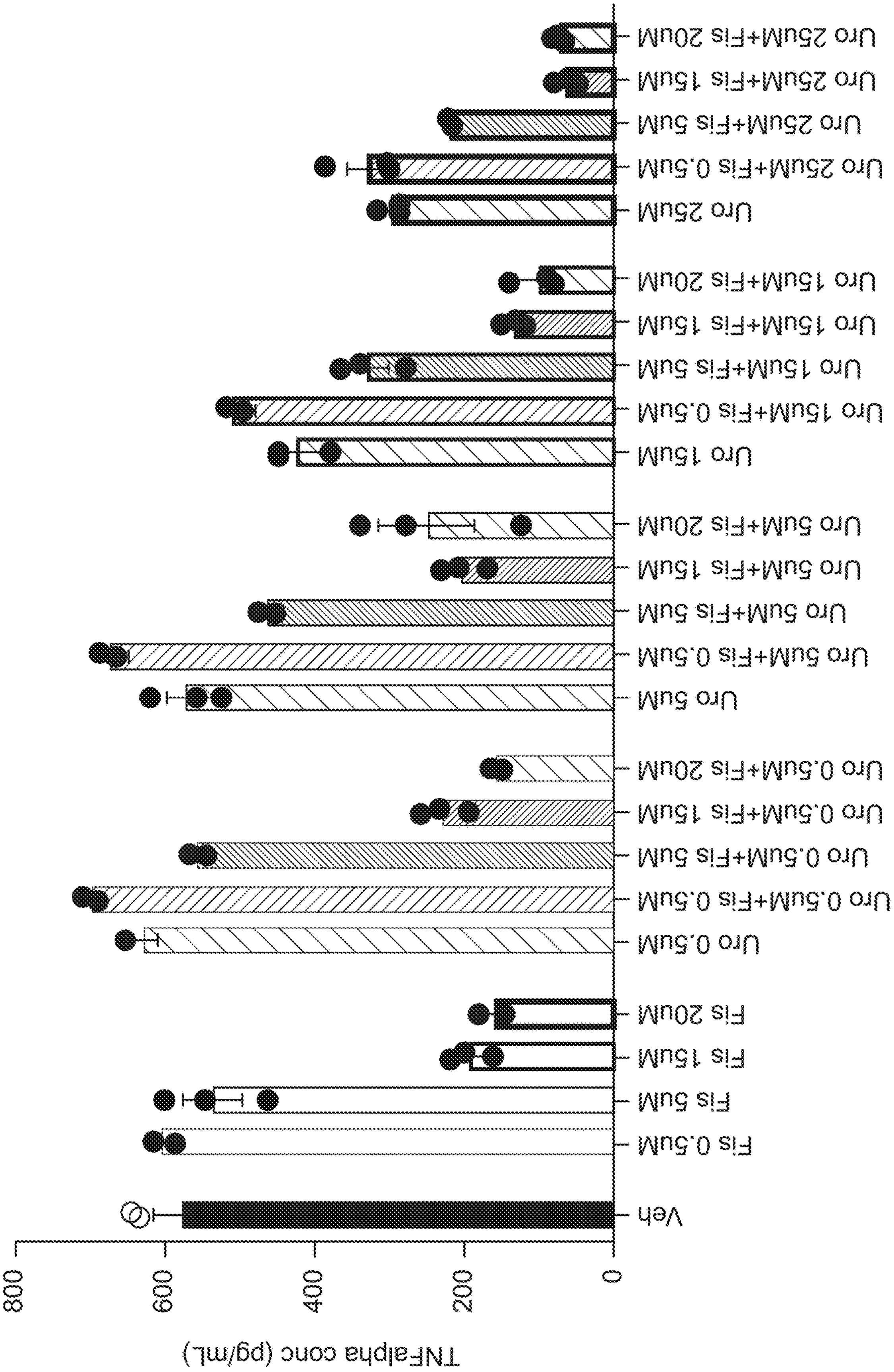
FIG. 5 shows TNFα levels secreted by BV2 microglial cells in response to varying doses of urolithin A and fisetin, alone or in combination.

BV2 microglial cells were next treated with 1 μg/mL of LPS for 5 hours in the presence of urolithin A and fisetin at different concentrations, alone or in combination (FIG. 5). Levels of TNFα secreted by the microglial cells into the conditioned cell media were measured using ELISA.

Figure 4B:
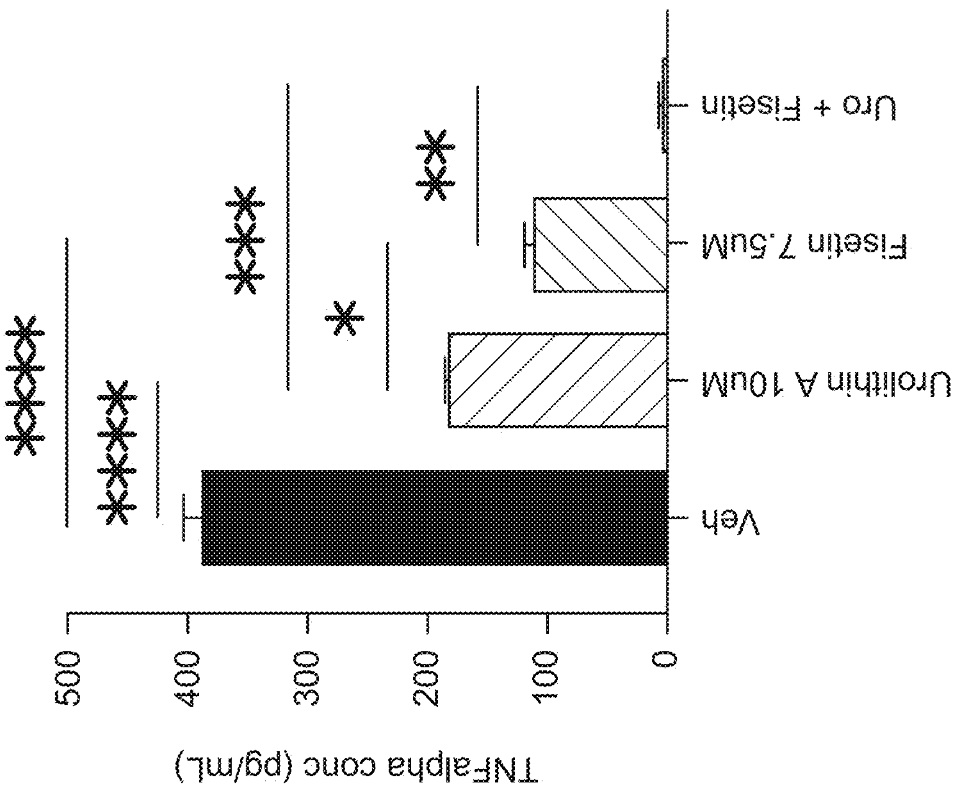

Co-treatment of urolithin A and fisetin dramatically reduced LPS-induced microglial pro-inflammatory activation, as measured by TNFα levels (FIG. 4B and FIG. 5). The combination of urolithin A and fisetin unexpectedly and dramatically increases the ability of fisetin to reduce LPS-induced microglial pro-inflammatory activation, as measured by TNFα levels, significantly beyond fisetin, alone. The combination led to a more than additive effect in the reduction of LPS-induced microglial pro-inflammatory activation. Specifically, as shown in FIG. 4B, while Fisetin alone significantly reduced TNFα levels by roughly 75% in LPS-treated BV2 microglia cells, the combination of urolithin A at 10 μM and fisetin at 7.5 μM reduced TNFα levels to almost under-detectable levels, suggesting a synergistic effect with the co-treatment.

Results as described herein demonstrate that combining urolithin A and fisetin promote the beneficial role of microglia in mediating Aß clearance while at the same time restrict harmful microglial pro-inflammatory activation and the combination dramatically enhances the two different therapeutic benefits compared to single treatment with either urolithin A or fisetin, alone.

Figure 6B:
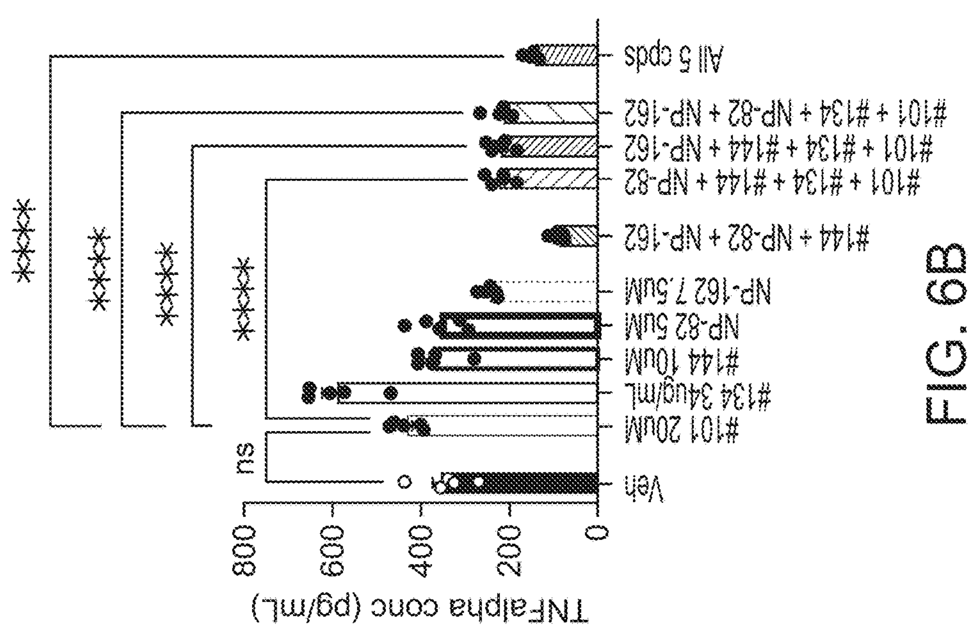
FIGS. 6A-6E show TNFα concentration upon treatment with nicotinamide riboside (#101) at 20 μM, cat's claw (#134) at 34 μg/mL, urolithin A (#144) at 10 μM, fisetin (NP-82) at 5 μM or quercetin (NP-162) at 7.5 μM, alone or in combination.
Figure 6A:
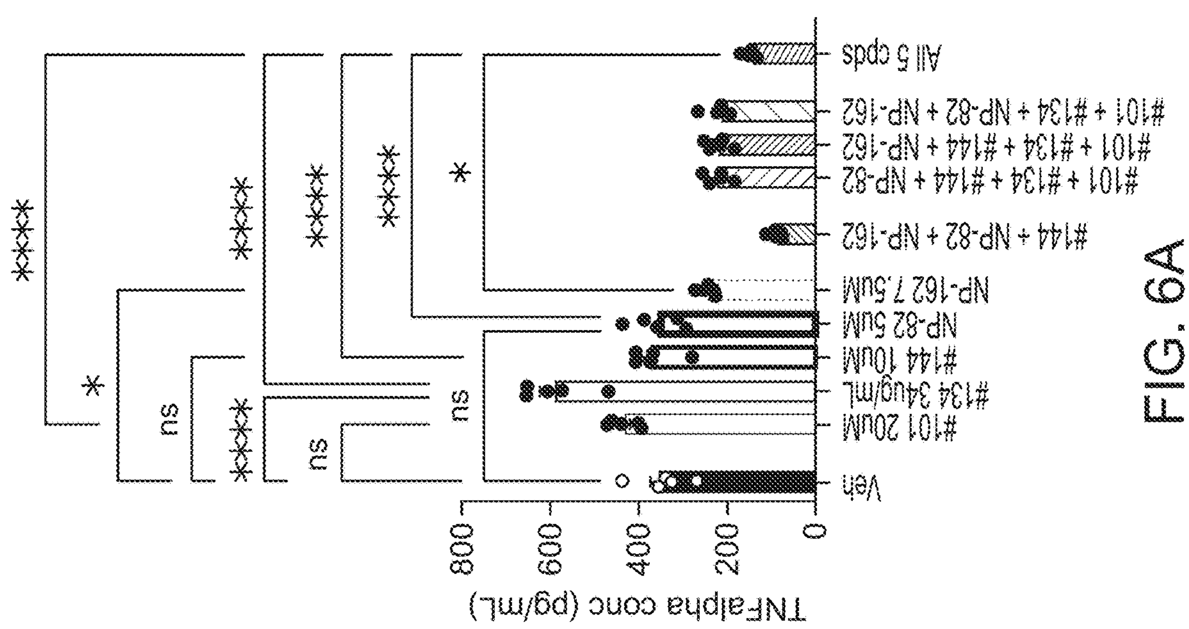
Figure 6D:
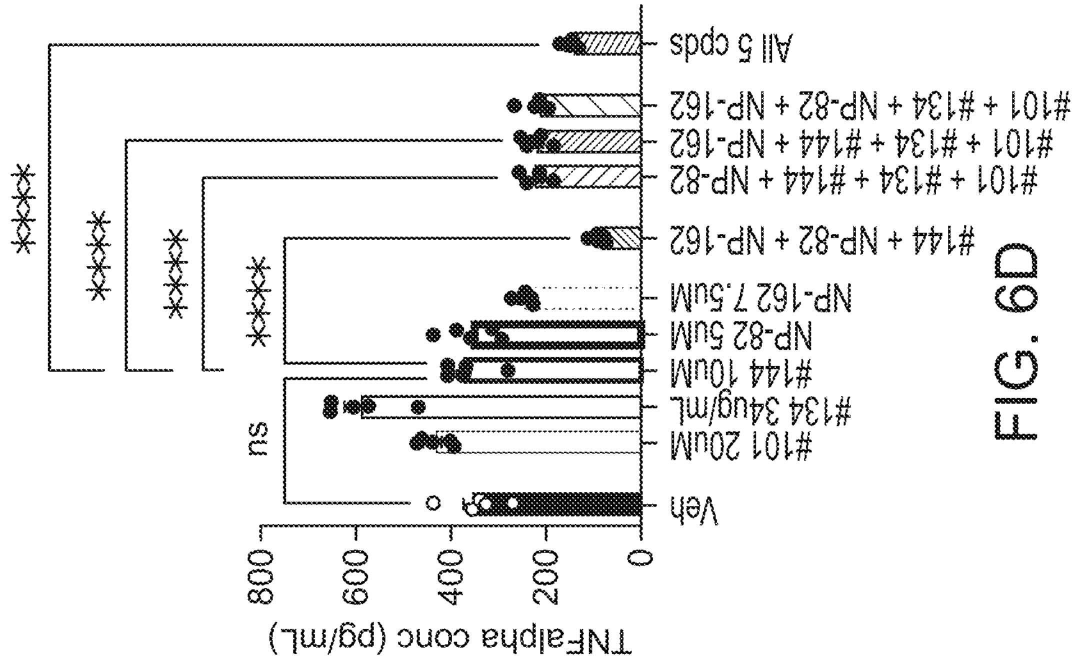
Figure 6C:
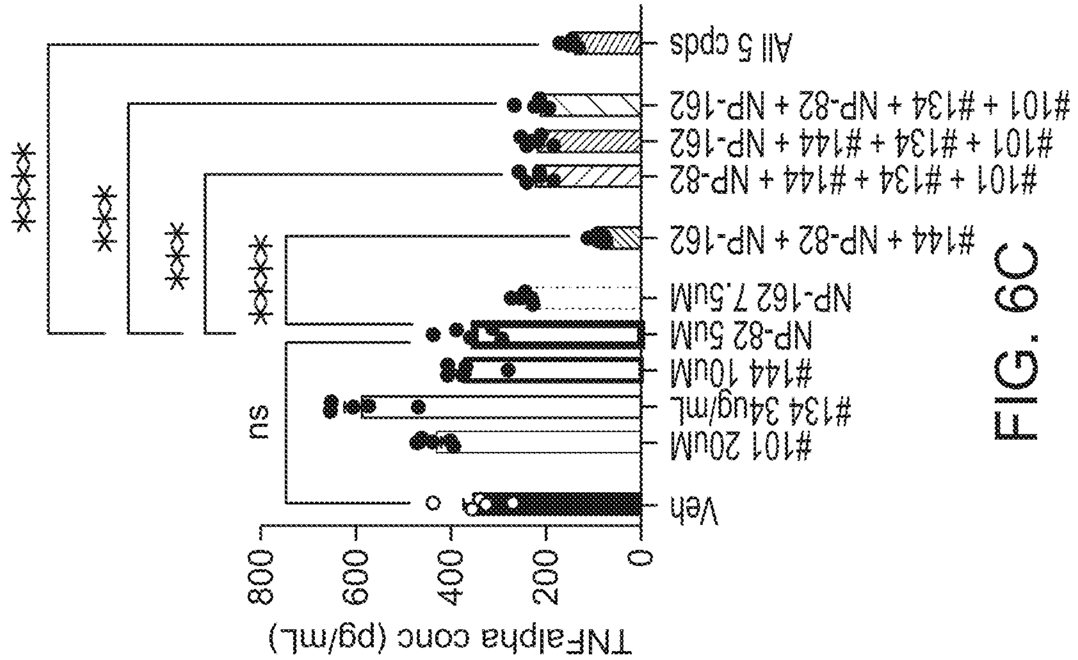
Figure 7A:
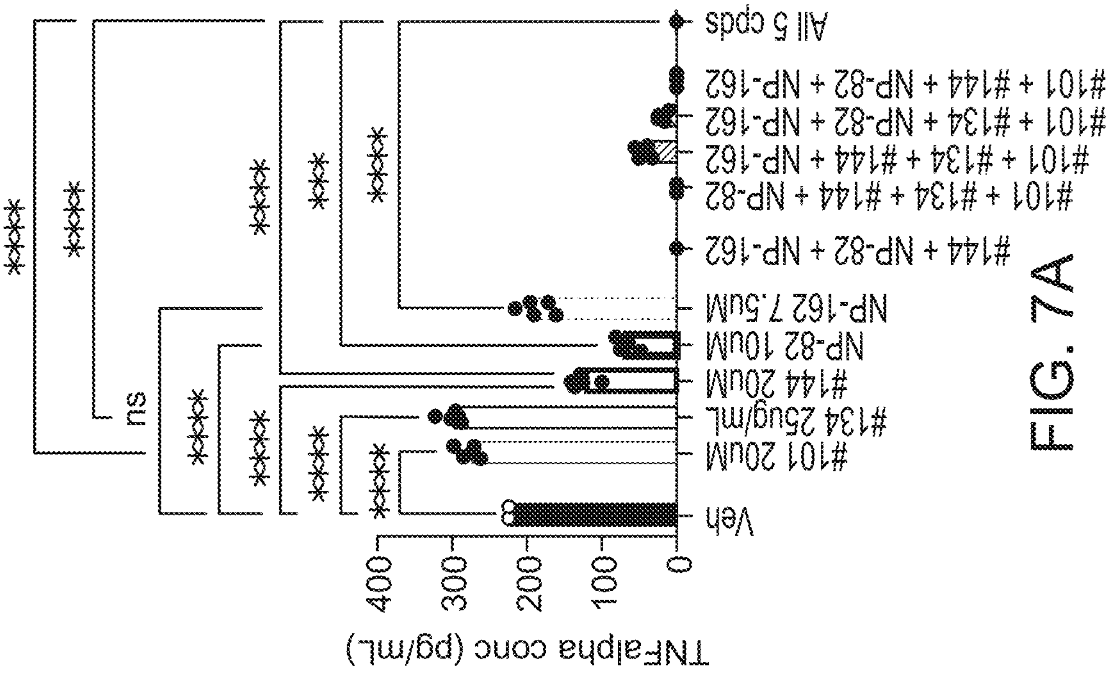
FIGS. 7A-7C show TNFα concentration upon treatment with nicotinamide riboside (#101) at 20 μM, cat's claw (#134) at 25 μg/mL, urolithin A (#144) at 20 μM, fisetin (NP-82) at 10 μM or quercetin (NP-162) at 7.5 μM, alone or in combination.
Figure 6E:
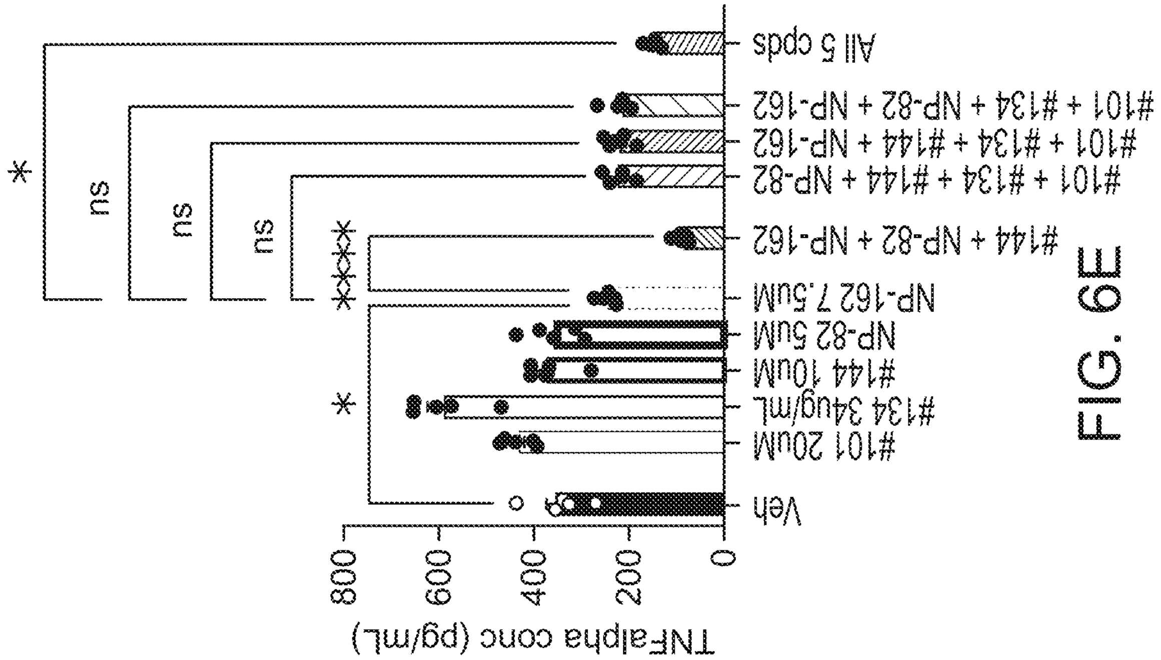
Figure 7C:
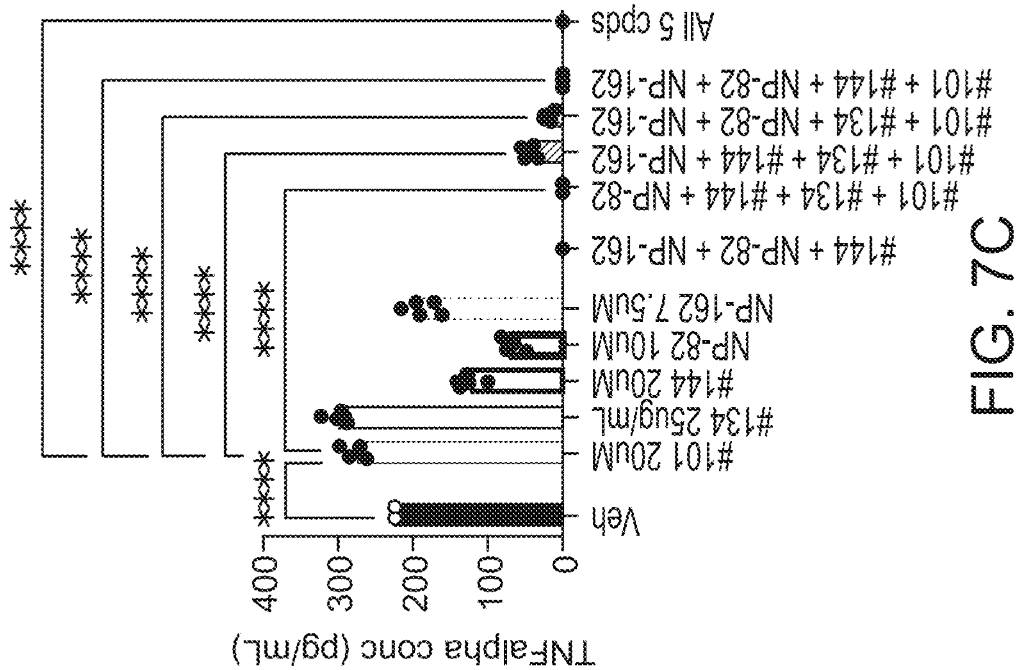
Figure 7B:
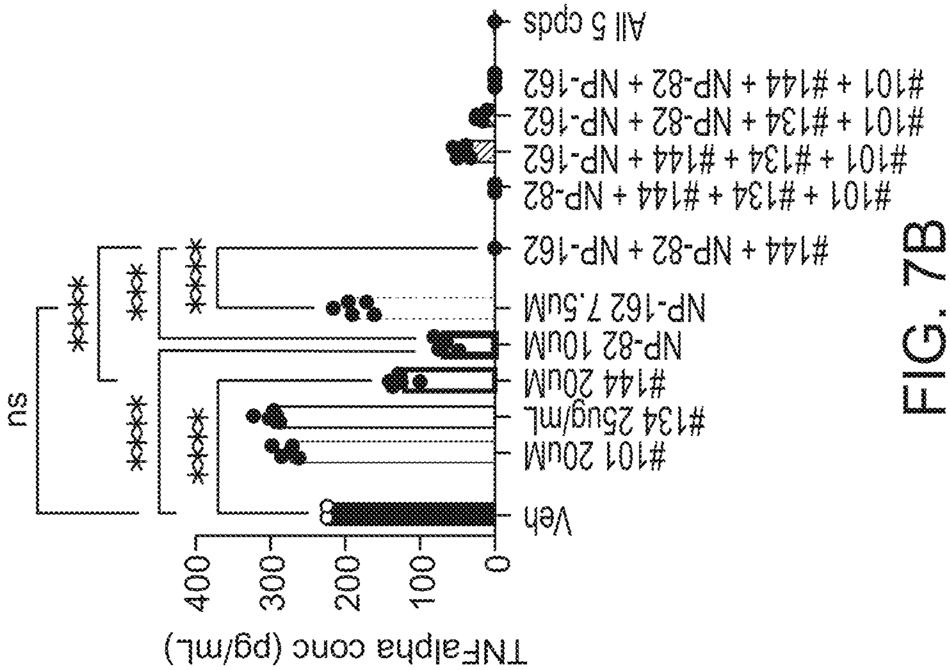
Figure 8:
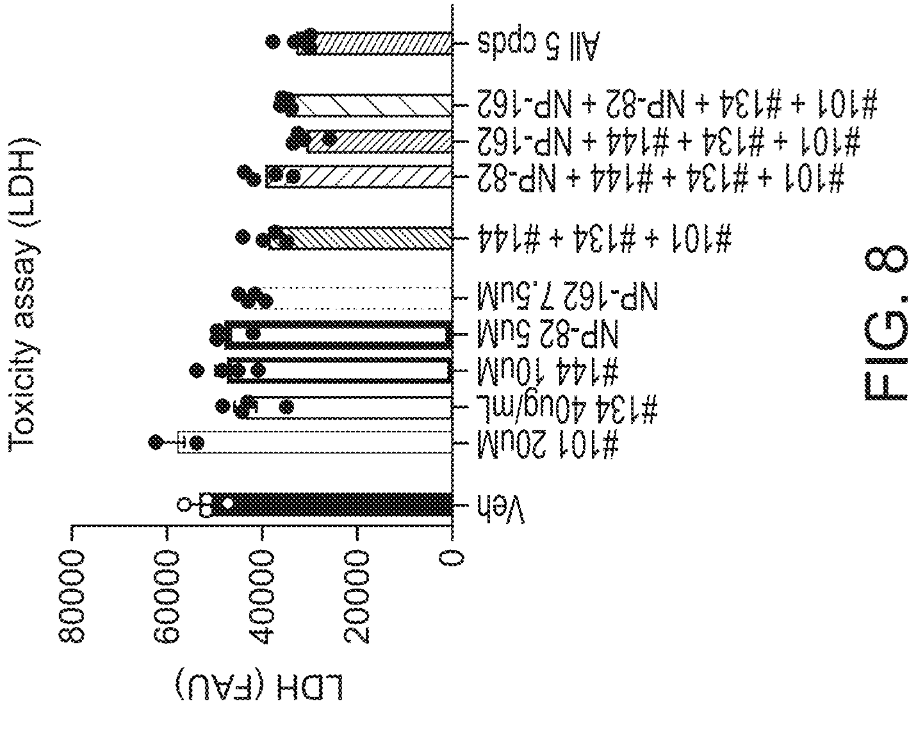
FIG. 8 shows toxicity upon treatment with nicotinamide riboside (#101) at 20 μM, cat's claw (#134) at 40 μg/mL, urolithin A (#144) at 10 μM, fisetin (NP-82) at 5 μM or quercetin (NP-162) at 7.5 μM, alone or in combination.

Example 2: Effects of Urolithin a, Fisetin, Nicotinamide Riboside, Cat's Claw, and Quercetin on Microglial Aß Clearance and the Release of Pro-Inflammatory Cytokine Effects of urolithin A, fisetin, nicotinamide riboside, cat's claw, and quercetin, alone or in combination, on TNFα concentration were assessed (FIGS. 6A-6E and 7A-7C). BV2 microglial cells were converted to a pro-inflammatory activation state by acute treatment with 1 μg/mL of Lipopolysaccharide (LPS) for 5 hours in the presence of a vehicle or nicotinamide riboside (#101), cat's claw (#134), urolithin A (#144), fisetin (NP-82) or quercetin (NP-162), alone or in combination. Effects on inflammation were assessed by measuring levels of TNFα, via an ELISA assay on the conditioned cell media. As shown in FIGS. 6A-6E and 7A-7C, the combination of the five agents was able to reduce TNFα release to a greater extent compared to each agent alone. Moreover, as shown in FIGS. 6C-6E, urolithin A (#144), fisetin (NP-82) and quercetin (NP-162) in combination can reduce TNFα release to a greater extent compared to each of the three agents alone. Toxicity was assessed by monitoring the levels of lactate dehydrogenase released in the conditioned media, and the results demonstrated that viability was not impacted by the treatments (FIG. 8).

Figure 9:
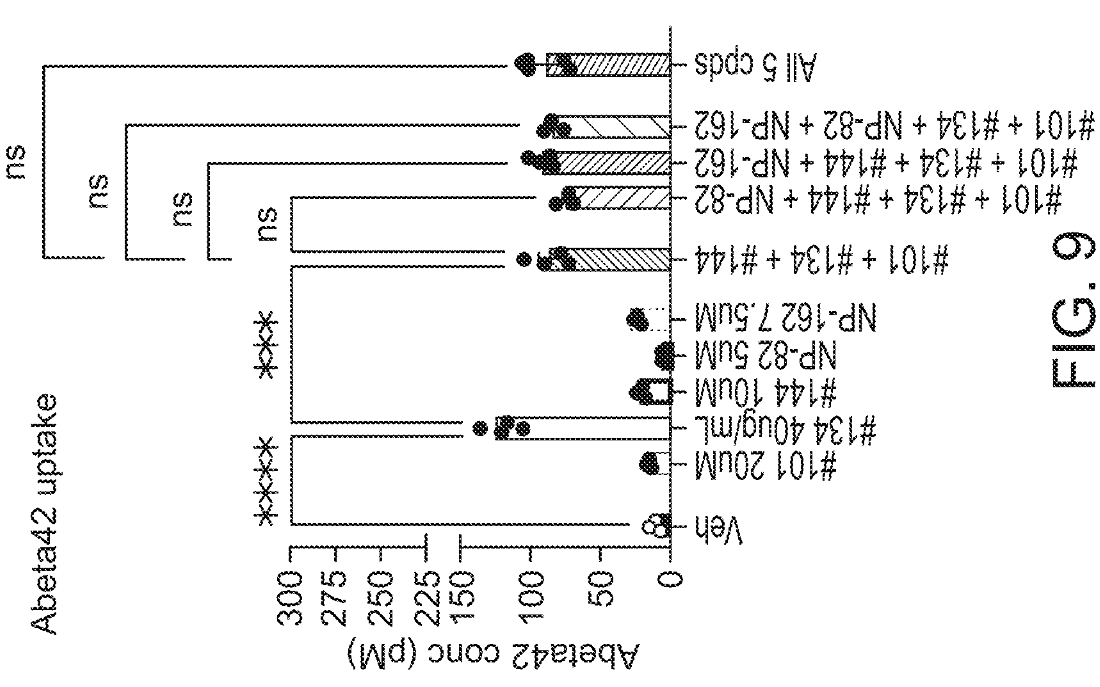
FIG. 9 shows Aβ uptake upon treatment with nicotinamide riboside (#101) at 20 μM, cat's claw (#134) at 40 μg/mL, urolithin A (#144) at 10 μM, fisetin (NP-82) at 5 μM or quercetin (NP-162) at 7.5 μM, alone or in combination.
Figure 10C:
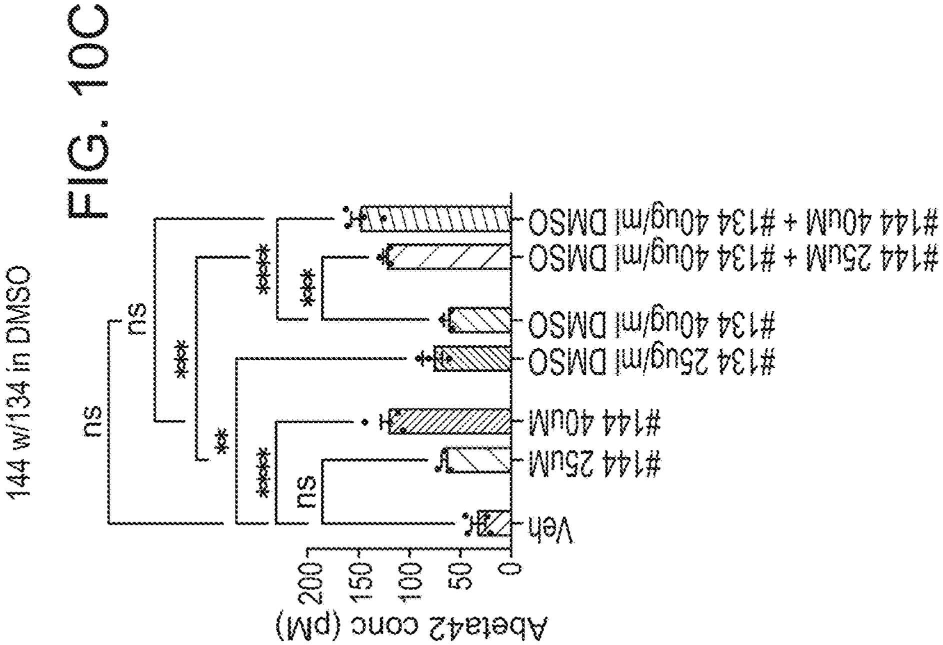
FIG. 10C shows Aβ uptake upon treatment with cat's claw (#134) at 25 μg/mL or 40 μg/mL in DMSO in combination with urolithin A (#144).
Figure 10A:
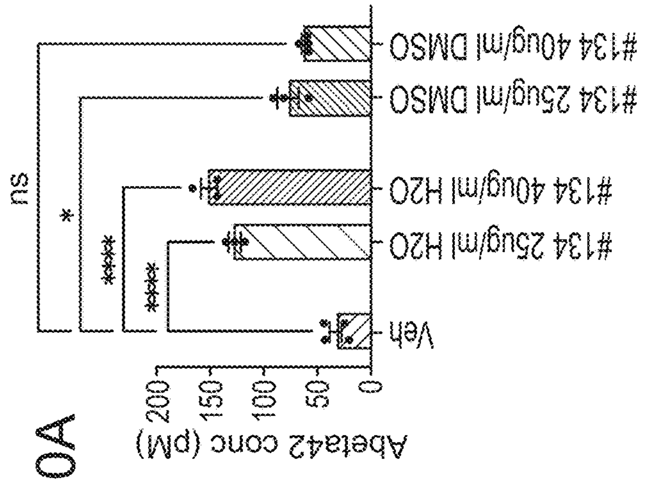
FIG. 10A shows Aβ uptake upon treatment with cat's claw at 25 μg/mL or 40 μg/mL in water or DMSO.
Figure 10B:
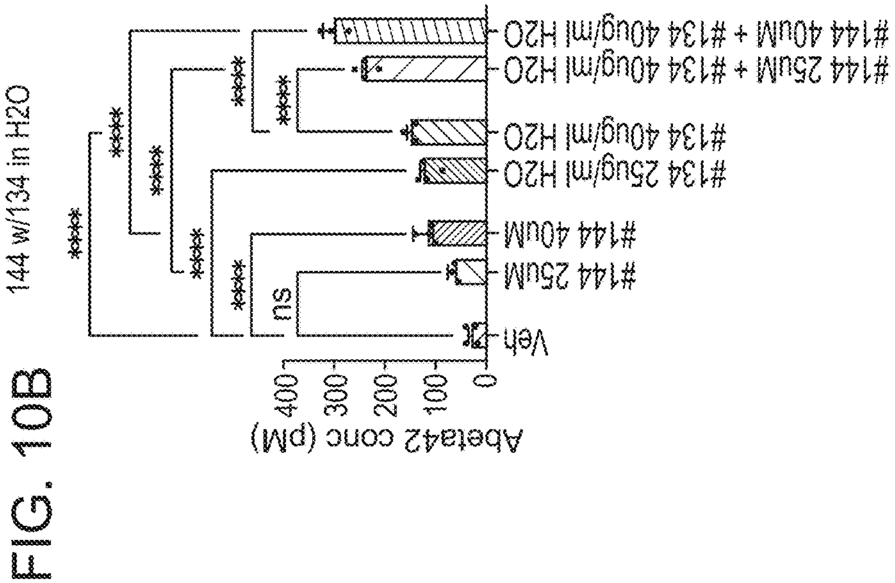
FIG. 10B shows Aβ uptake upon treatment with cat's claw (#134) at 25 μg/mL or 40 μg/mL in water in combination with urolithin A (#144) at 25 μM or 40 μM.
Figure 11A:
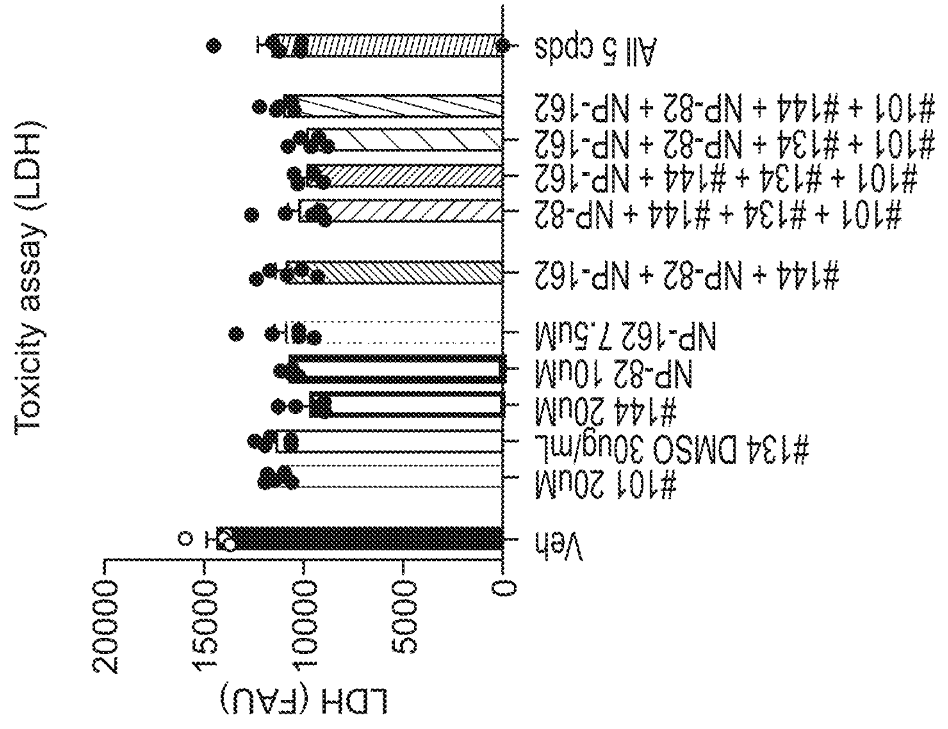
FIG. 11A shows toxicity upon treatment with nicotinamide riboside (#101) at 20 μM, cat's claw (#134) at 30 μg/mL, urolithin A (#144) at 20 μM, fisetin (NP-82) at 10 μM or quercetin (NP-162) at 7.5 μM, alone or in combination.
Figure 11B:
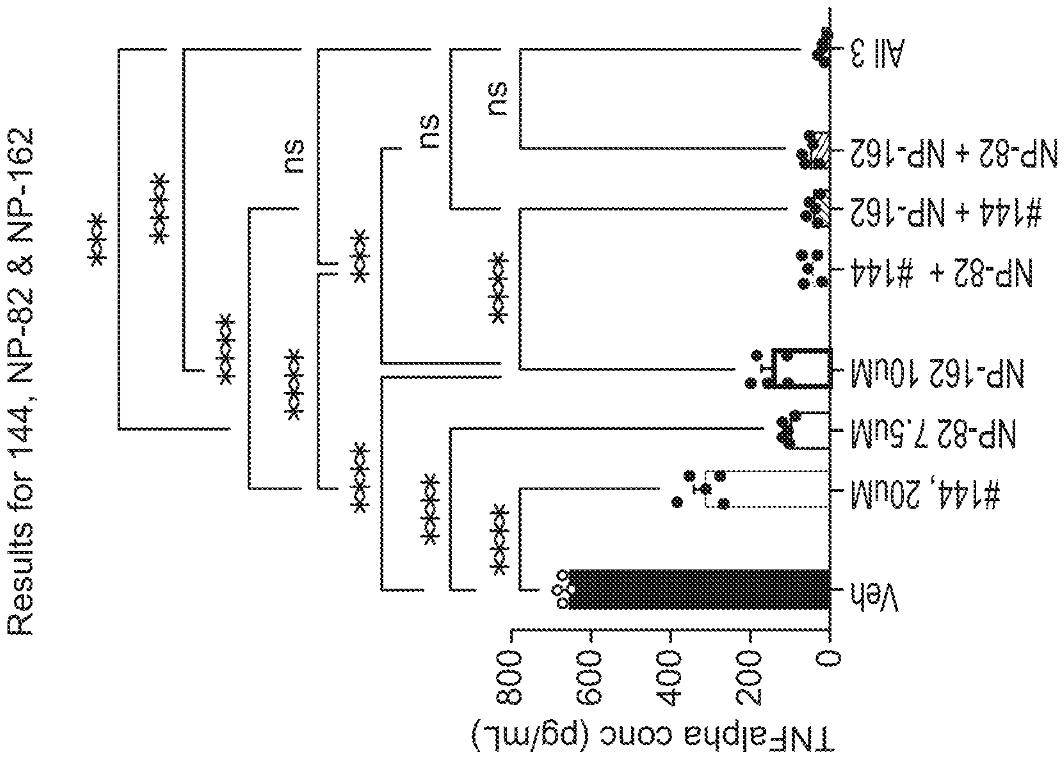
FIGS. 11B-11D show TNFα levels upon treatment with urolithin A (#144) at 20 μM, fisetin (NP-82) at 7.5 μM or quercetin (NP-162) at 10 μM, and cat's claw (#134) at 30 μg/mL, alone or in combination.
Figure 11C:
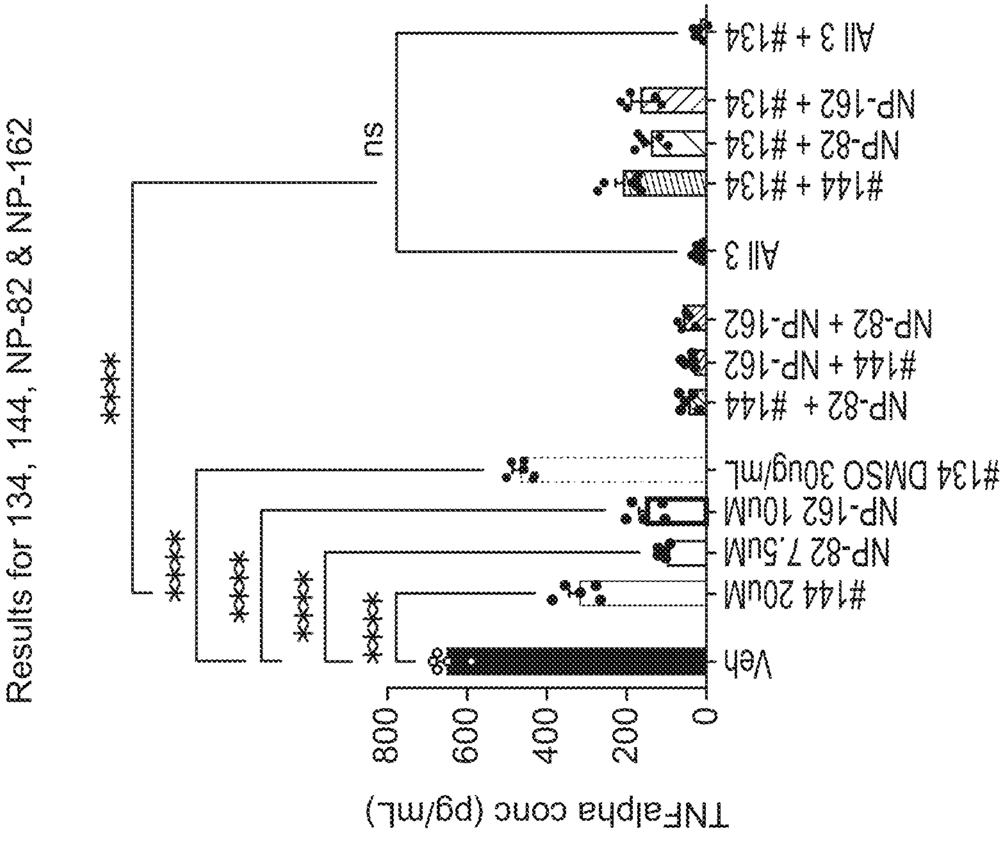
Figure 11D:
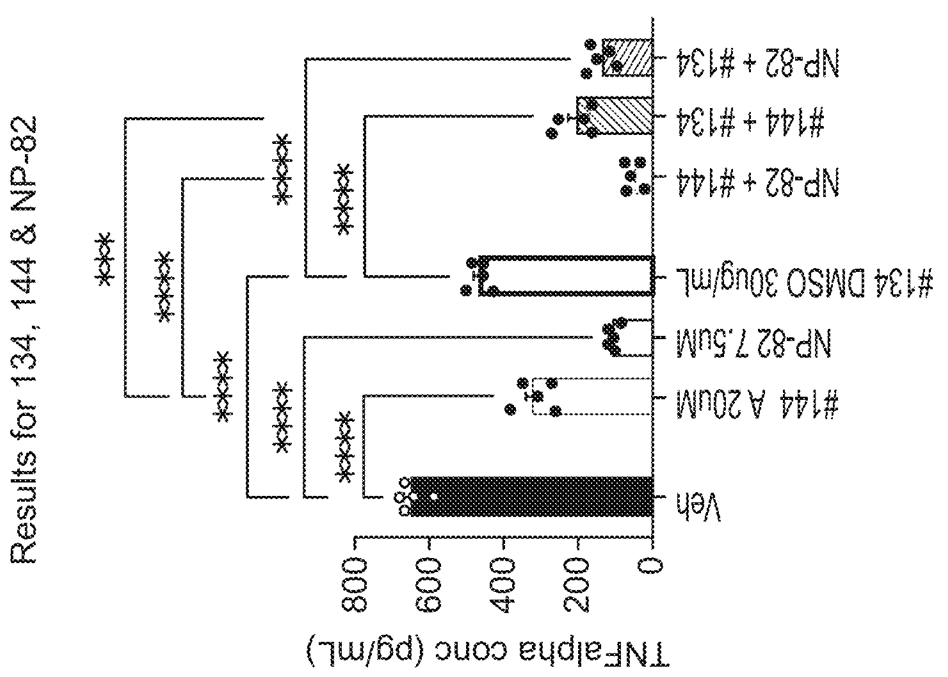
Figure 12B:
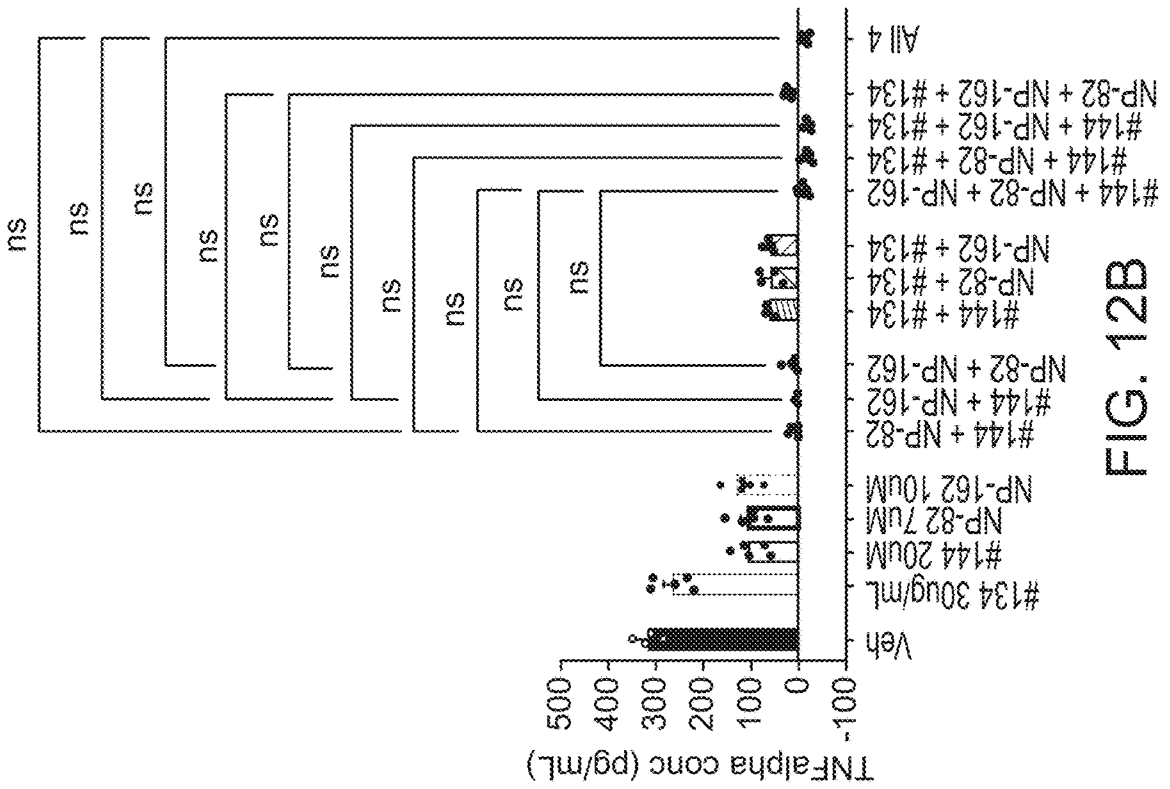
FIGS. 12A-12F show TNFα levels upon treatment with cat's claw (#134) at 30 μg/mL, urolithin A (#144) at 20 μM, fisetin (NP-82) at 7 μM or quercetin (NP-162) at 10 μM, alone or in combination.
Figure 12A:
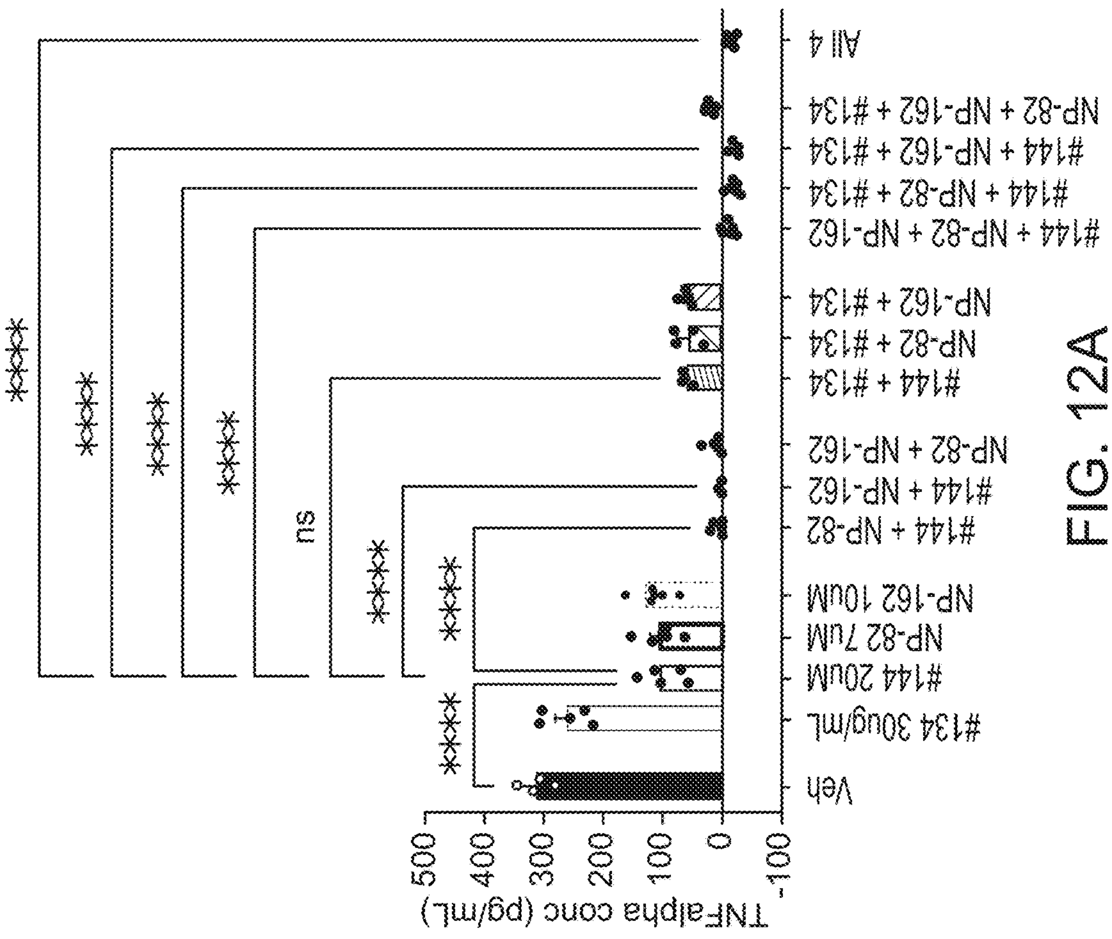
Figure 12D:
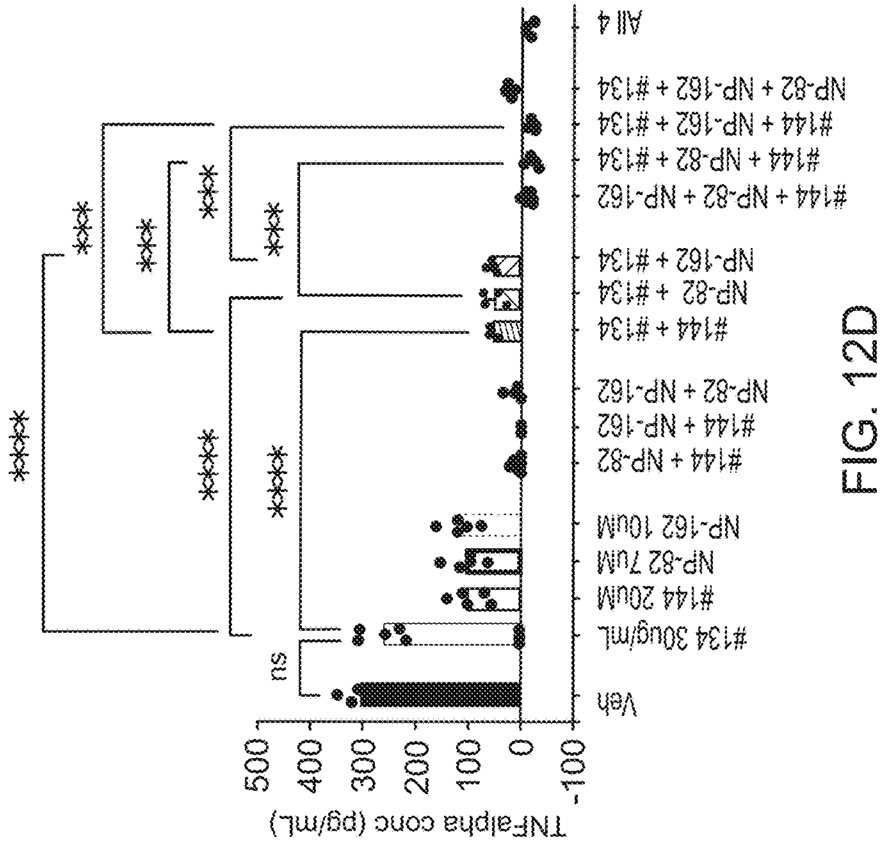
Figure 12C:
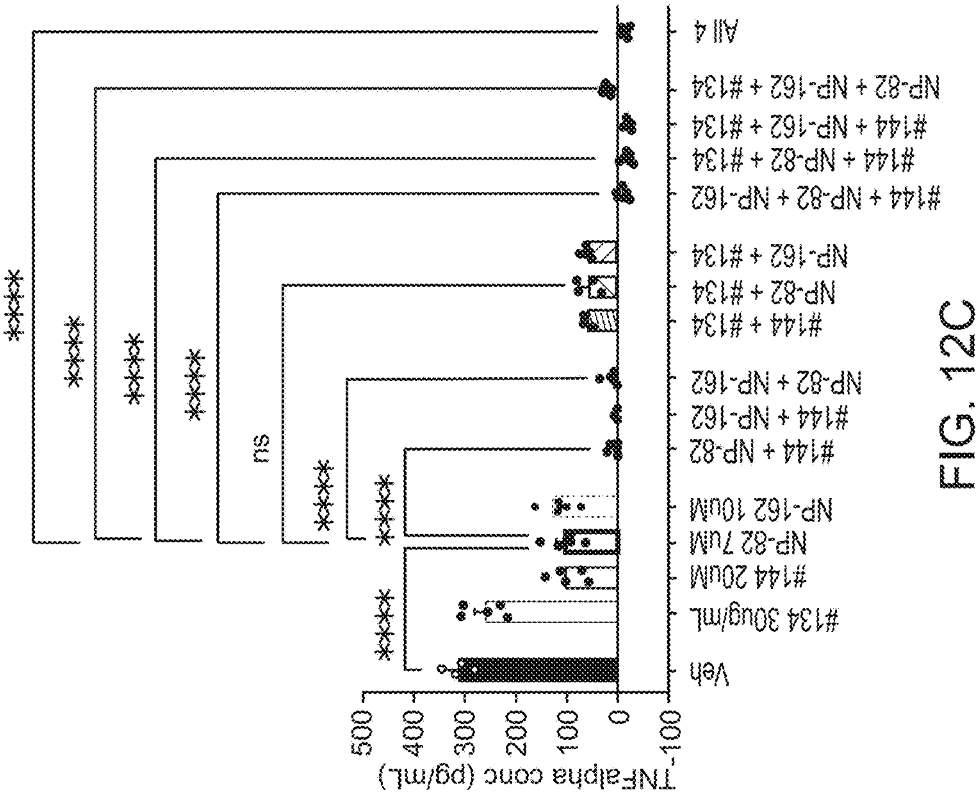
Figure 12F:
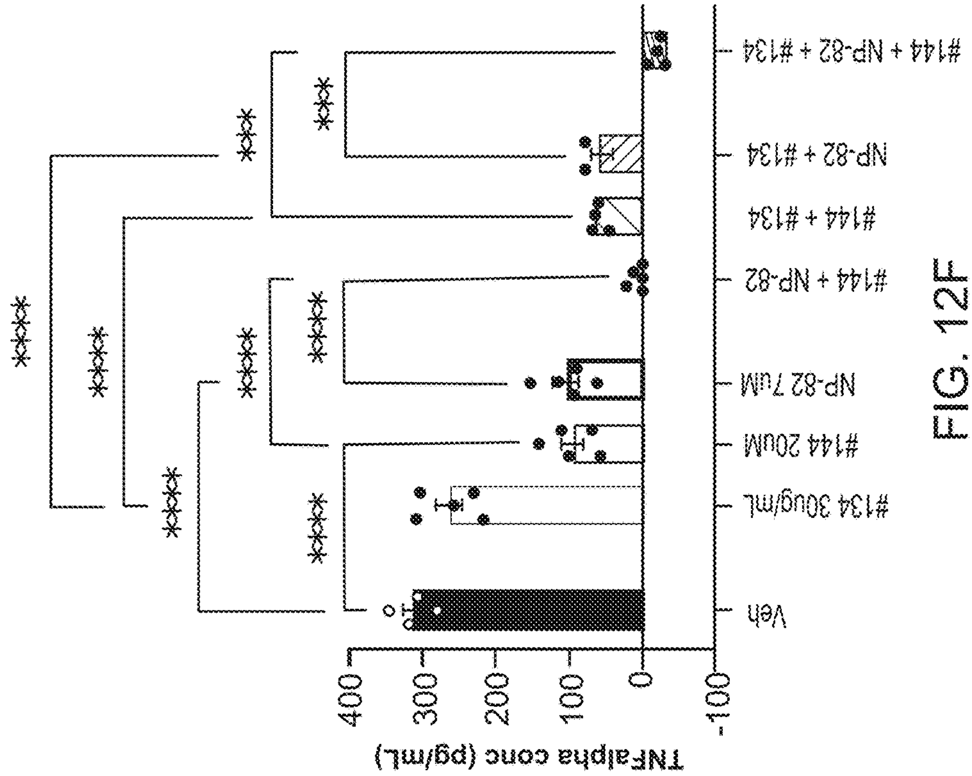
Figure 12E:
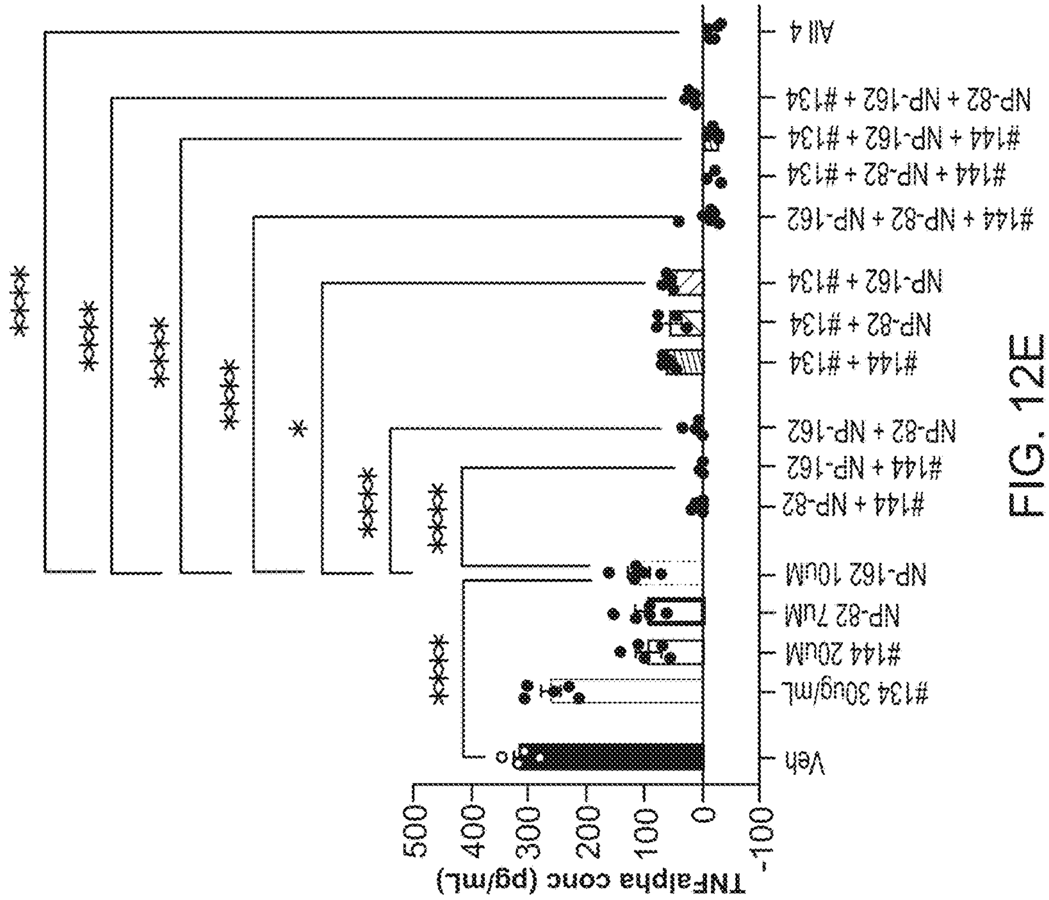

The ability of the agents, alone or in combination, to increase microglial Aß uptake was also assessed (FIG. 9). Cat's claw significantly increased Aß uptake compared to vehicle (FIGS. 9 and 10A). Furthermore, the combination of cat's claw (#134) and urolithin A (#144) was able to increase Aß uptake more than cat's claw and urolithin A alone (FIGS. 10B and 10C). FIGS. 11B-11D and FIGS. 12A-12F show TNFα levels in response to treatment with cat's claw (#134), urolithin A (#144), fisetin (NP-82) and quercetin (NP-162), alone or in various combinations. As shown in FIG. 12A-12F, the combination of urolithin A, fisetin and quercetin reduced TNFα levels to a greater extent than urolithin A, fisetin, or quercetin alone; the combination of urolithin A, fisetin and cat's claw reduced TNFα levels to a greater extent than urolithin A, fisetin, or cat's claw alone.

Figure 13B:
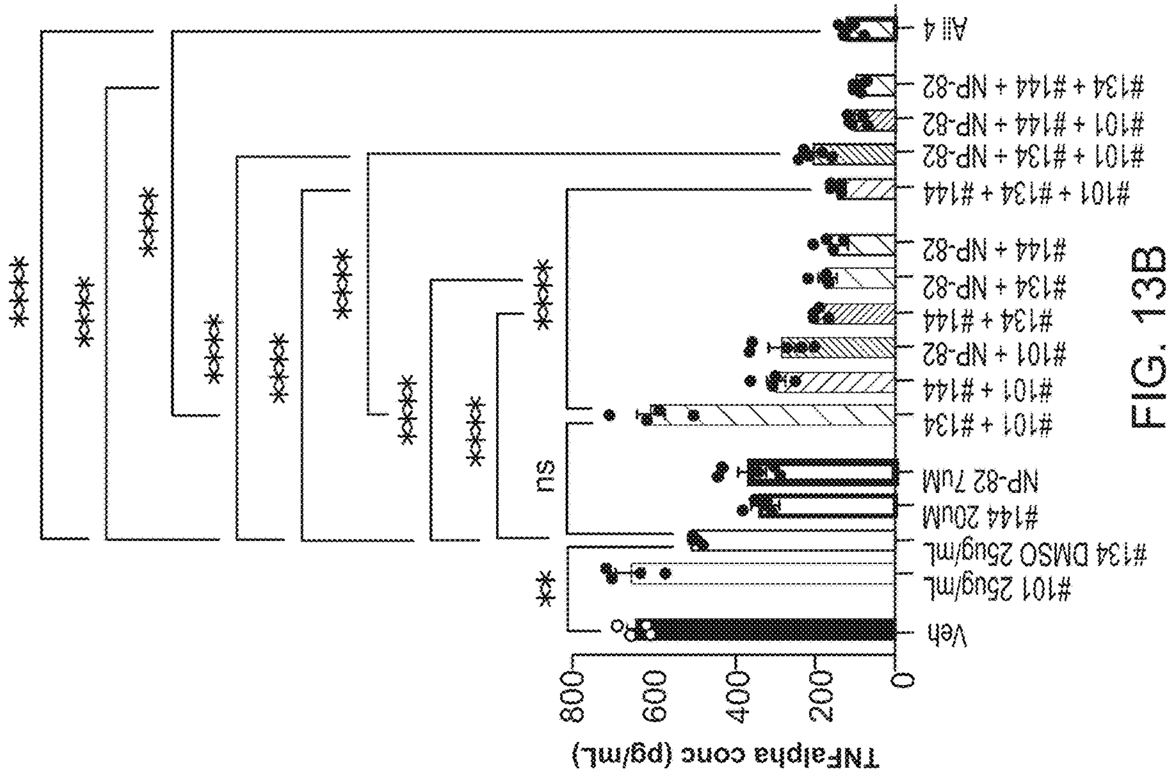
FIGS. 13A-13E show TNFα levels upon treatment with nicotinamide riboside (#101) at 25 μM, cat's claw (#134) at 30 μg/mL, urolithin A (#144) at 20 μM, and fisetin (NP-82) at 7 μM, alone or in combination.
Figure 13A:
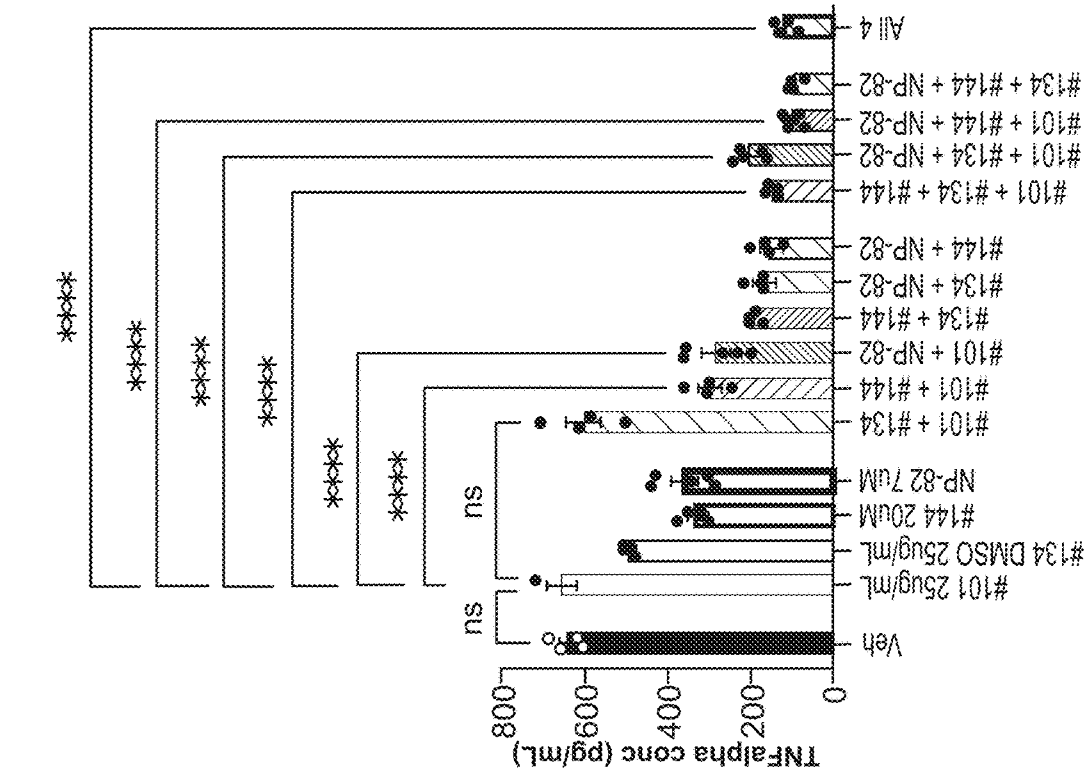
Figure 13D:
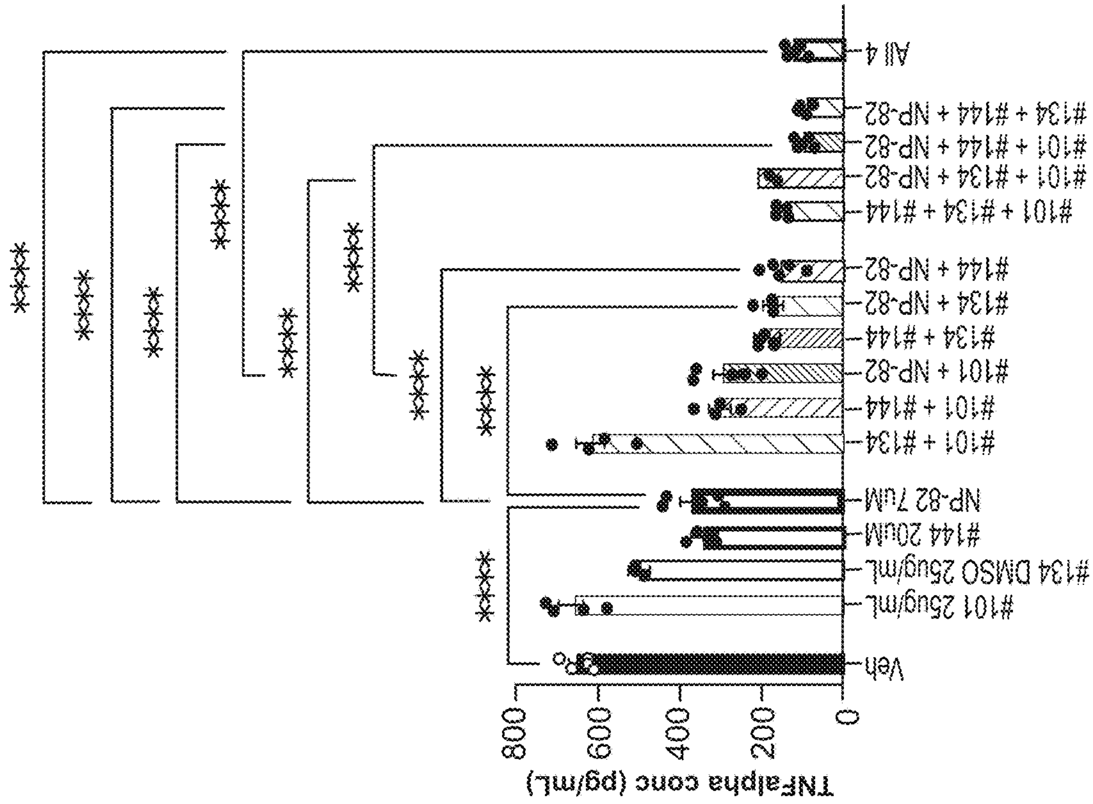
Figure 13C:
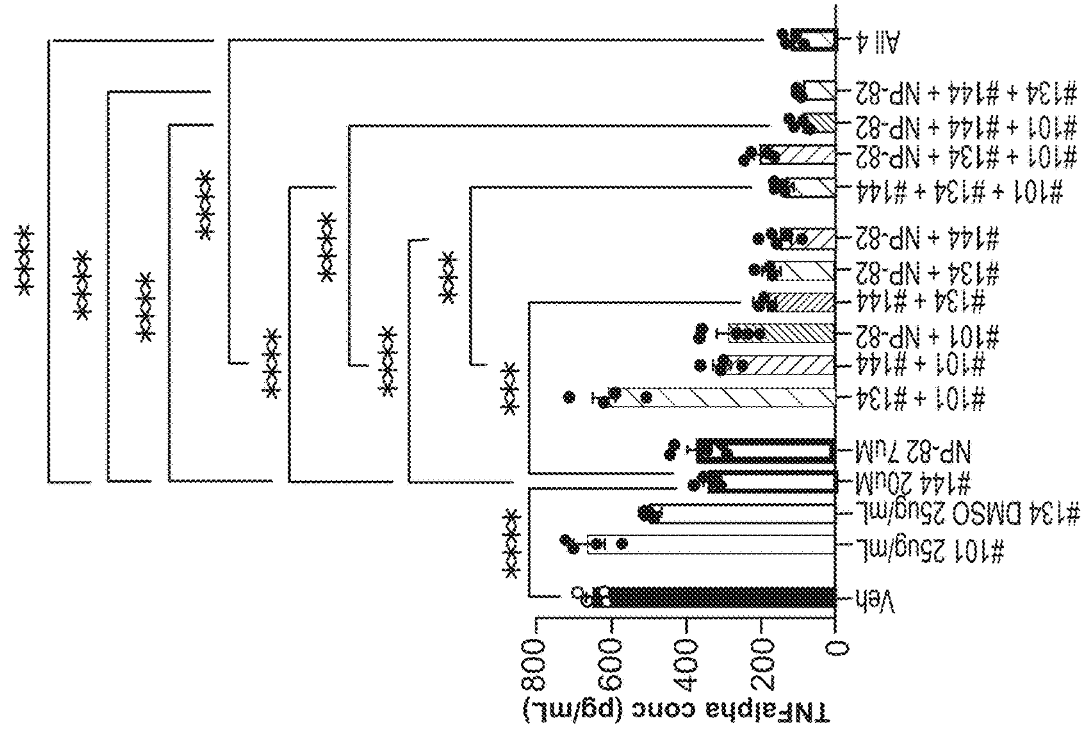
Figure 13E:
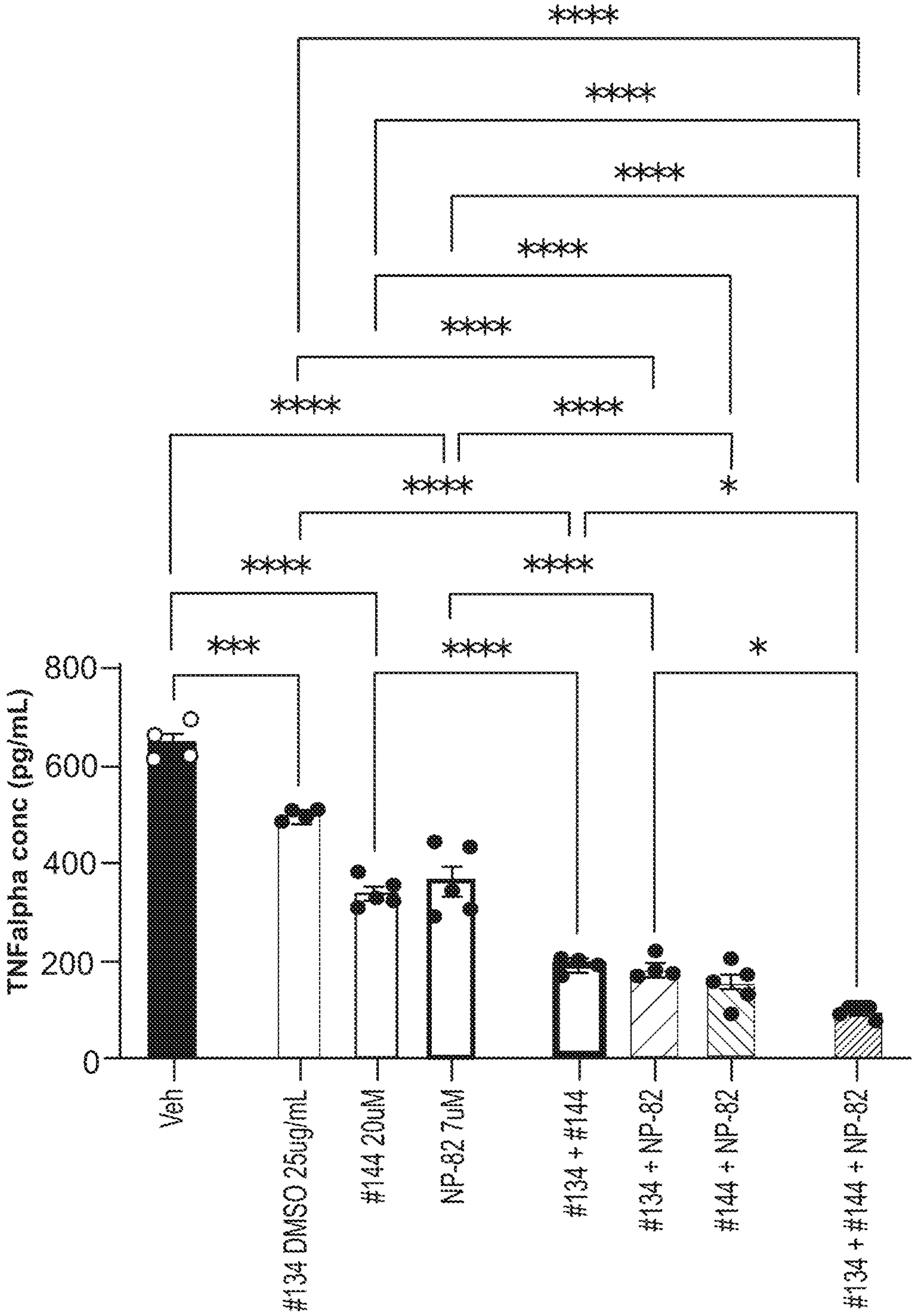

FIGS. 13A-13E show TNFα levels in response to treatment with nicotinamide riboside (#101), cat's claw (#134), urolithin A (#144), and fisetin (NP-82), alone or in various combinations. These results show that the combination of urolithin A, fisetin and nicotinamide riboside reduced TNFα levels to a greater extent than urolithin A, fisetin, or nicotinamide riboside alone; the combination of urolithin A, fisetin and cat's claw reduced TNFα levels to a greater extent than urolithin A, fisetin, and cat's claw alone. Further, the combination of urolithin A, fisetin and nicotinamide riboside reduced TNFα levels to a greater extent than the combination of urolithin A and nicotinamide riboside or the combination of fisetin and nicotinamide riboside (FIGS. 13C and 13D). The combination of urolithin A, fisetin and cat's claw reduced TNFα levels to a greater extent than the combination of urolithin A and cat's claw or the combination of fisetin and cat's claw (FIG. 13E).

What is claimed is:

1. A composition comprising:

urolithin A in an amount that is from about 1 mg to about 2500 mg;

fisetin in an amount that is from about 0.5 mg to about 2500 mg; and quercetin in an amount that is about 1 mg to about 2500 mg.

2. The composition of claim 1, wherein the composition is formulated for oral administration.

3. The composition of claim 2, wherein the composition is in the form of a powder.

4. The composition of claim 2, wherein the composition is in the form of a capsule.

5. The composition of claim 2, wherein the composition is in the form of a tablet.

6. The composition of claim 1, wherein the composition comprises urolithin A in an amount that is from about 1 mg to about 1000 mg.

7. The composition of claim 6, wherein the composition comprises urolithin A in an amount that is about 1 mg, about 10 mg, about 50 mg, about 75 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg.

8. The composition of claim 7, wherein the composition comprises urolithin A in an amount that is about 100 mg.

9. The composition of claim 1, wherein the composition comprises fisetin in an amount that is from about 50 mg to about 300 mg.

10. The composition of claim 1, wherein the composition comprises quercetin in an amount that is from about 50 mg to about 800 mg.

11. The composition of claim 1, comprising:

urolithin A in an amount that is from about 1 mg to about 1000 mg;

fisetin in an amount that is from about 50 mg to about 300 mg; and quercetin in an amount that is from about 50 mg to about 800 mg.

12. The composition of claim 11, wherein the composition is formulated for oral administration.

13. The composition of claim 12, wherein the composition is in the form of a powder.

14. The composition of claim 12, wherein the composition is in the form of a capsule.

15. The composition of claim 12, wherein the composition is in the form of a tablet.

16. A kit comprising a composition of claim 1 and instructions for administration.

17. The kit of claim 16, wherein the instructions provide direction to administer the composition to the subject once daily.

* * * * *